United States Patent
Lin

(10) Patent No.: US 10,151,760 B2
(45) Date of Patent: Dec. 11, 2018

(54) METHOD FOR VALIDATING EXISTENCE OF URINARY EXOSOME, NON-INVASIVE METHOD FOR IDENTIFYING UROTHELIAL CANCER, AND METHOD FOR PREDICTING RECURRENCE AND PROGRESSION OF UROTHELIAL CANCER PATIENT AFTER TREATMENT

(71) Applicant: China Medical University, Taichung (TW)

(72) Inventor: Shih-Yi Lin, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 73 days.

(21) Appl. No.: 15/343,230

(22) Filed: Nov. 4, 2016

(65) Prior Publication Data
US 2017/0350902 A1 Dec. 7, 2017

(30) Foreign Application Priority Data
Jun. 6, 2016 (TW) .............................. 105117855 A

(51) Int. Cl.
*G01N 24/00* (2006.01)
*G01N 33/68* (2006.01)

(52) U.S. Cl.
CPC ..... *G01N 33/6851* (2013.01); *G01N 2800/52* (2013.01); *G01N 2800/54* (2013.01); *G01N 2800/7028* (2013.01)

(58) Field of Classification Search
None
See application file for complete search history.

(56) References Cited

U.S. PATENT DOCUMENTS

2012/0283123 A1* 11/2012 Sarwal ................ C12Q 1/6883
506/9

OTHER PUBLICATIONS

Fernandez-Llama, P. et al. Tamm-Horsfall protein and urinary exosome isolation, Kidney International, 2010, vol. 77, pp. 736-742 (Year: 2010).*
Pisitkum, T. et al. Identification and proteomic profiling of exosomes in human urine, PNAS, 2004, vol. 101(36), pp. 13368-13373 (Year: 2004).*
Wu, Jing, et al. Urinary proteomics as a novel tool for biomarker discovery in kidney diseases, Journal of Zhenjing University—Science B (Biomedicine & Biotechnology), 2010, vol. 11(4), pp. 227-237 (Year: 2010).*

* cited by examiner

*Primary Examiner* — Xiaoyun R Xu

(57) ABSTRACT

The present disclosure relates to a method for validating an existence of a urinary exosome including steps as follows. A urine sample is obtained from a subject. The urine sample is performing a serially centrifugation step to obtain a third precipitate. The third precipitate is resuspended with an extraction solvent to obtain a third mixture, and the third mixture is centrifuged to obtain a fourth supernatant. The fourth supernatant is analyzed by a mass spectrometry to detect whether there is a particular peptide therein.

6 Claims, 16 Drawing Sheets
(1 of 16 Drawing Sheet(s) Filed in Color)
Specification includes a Sequence Listing.

SEQUENCE LISTING

<160> NUMBER OF SEQ ID NOS: 6

<210> SEQ ID NO 1
<211> LENGTH: 32
<212> TYPE: PRT
<213> ORGANISM: Homo sapiens

<400> SEQUENCE: 1

Ala Ala Pro Glu Gln Ile Ala Ala Asp Ile Pro Glu Val Val Val Ser
1               5                   10                  15

Leu Ala Pro Lys His Pro Gly Ser Arg Lys Asn Met Ala Cys Tyr Cys
            20                  25                  30

<210> SEQ ID NO 2
<211> LENGTH: 34
<212> TYPE: PRT
<213> ORGANISM: Homo sapiens

<400> SEQUENCE: 2

Thr Leu Ala Ile Leu Ala Ala Ile Leu Leu Val Ala Leu Gln Ala Gln
1               5                   10                  15

Ala Glu Pro Gln Ala Arg Ala Asp Glu Val Ala Ala Ala Pro Glu Gln
            20                  25                  30

Ile Ala

<210> SEQ ID NO 3
<211> LENGTH: 34
<212> TYPE: PRT
<213> ORGANISM: Homo sapiens

<400> SEQUENCE: 3

Ala Asp Glu Val Ala Ala Ala Pro Glu Gln Ile Ala Ala Asp Ile Pro
1               5                   10                  15

Glu Val Val Val Ser Leu Ala Pro Lys His Pro Gly Ser Arg Lys Asn
            20                  25                  30

Met Ala

<210> SEQ ID NO 4
<211> LENGTH: 92
<212> TYPE: PRT
<213> ORGANISM: Homo sapiens

<400> SEQUENCE: 4

Arg Asn Ile Glu Thr Ile Ile Asn Thr Phe His Gln Tyr Ser Val Lys
1               5                   10                  15

Leu Gly His Pro Asp Thr Leu Asn Gln Gly Glu Phe Lys Glu Leu Val
            20                  25                  30

Arg Lys Asp Leu Gln Asn Phe Leu Lys Lys Glu Asn Lys Asn Glu Lys
        35                  40                  45

Val Ile Glu His Ile Met Glu Asp Leu Asp Thr Asn Ala Asp Lys Gln
    50                  55                  60

Leu Ser Phe Glu Glu Phe Ile Met Leu Met Ala Arg Leu Thr Trp Ala
65                  70                  75                  80

Ser His Glu Lys Met His Glu Gly Asp Glu Gly Pro
                85                  90

<210> SEQ ID NO 5
<211> LENGTH: 54
<212> TYPE: PRT
<213> ORGANISM: Homo sapiens

```
<400> SEQUENCE: 5

Ser Ala Ser Leu His Leu Pro Lys Leu Ser Ile Thr Gly Thr Tyr Asp
1               5                   10                  15

Leu Lys Ser Val Leu Gly Gln Leu Gly Ile Thr Lys Val Phe Ser Asn
            20                  25                  30

Gly Ala Asp Leu Ser Gly Val Thr Glu Glu Ala Pro Leu Lys Leu Ser
        35                  40                  45

Lys Ala Val His Lys Ala
    50

<210> SEQ ID NO 6
<211> LENGTH: 53
<212> TYPE: PRT
<213> ORGANISM: Homo sapiens

<400> SEQUENCE: 6

Lys Val Leu Lys Gln Val His Pro Asp Thr Gly Ile Ser Ser Lys Ala
1               5                   10                  15

Met Gly Ile Met Asn Ser Phe Val Asn Asp Ile Phe Glu Arg Ile Ala
            20                  25                  30

Gly Glu Ala Ser Arg Leu Ala His Tyr Asn Lys Arg Ser Thr Ile Thr
        35                  40                  45

Ser Arg Glu Ile Gln
    50
```

METHOD FOR VALIDATING EXISTENCE OF URINARY EXOSOME, NON-INVASIVE METHOD FOR IDENTIFYING UROTHELIAL CANCER, AND METHOD FOR PREDICTING RECURRENCE AND PROGRESSION OF UROTHELIAL CANCER PATIENT AFTER TREATMENT

RELATED APPLICATIONS

This application claims priority to Taiwan Application Serial Number 105117855, filed Jun. 6, 2016, which is herein incorporated by reference.

SEQUENCE LISTING

The sequence listing submitted via EFS, in compliance with 37 CFR § 1.52(e)(5), is incorporated herein by reference. The sequence listing text file submitted via EFS contains the file "CP-3304-US_SequenceListing", created on Nov. 2, 2016, which is 3,409 bytes in size.

BACKGROUND

Technical Field

The present disclosure relates to a method for validating an existence of an exosome and applications thereof. More particularly, the present disclosure relates to a method for validating the existence of a urinary exosome and the applications thereof.

Description of Related Art

An urothelium (also called the transitional epithelium) is the lining on the inside of the bladder, ureters and urethra, as well as the renal pelvis (the part of the kidney where urine collects). An urothelial cancer (UC) is derived from lesions of the urothelium accounting for the majority of urinary tract tumors, which includes carcinomas of the bladder, ureters, and renal pelvis. The UC is the ninth most common malignancy worldwide.

Current diagnoses of the UC rely on a urine cytology, a urography (including intravenous urography (IVU) and CT-urography), and a cystoscopy aided by biopsy. Though the urine cytology and the urography are non-invasive, the sensitivity of these tests varies with the UC location and grade by more than 30%. The cystoscopy with biopsy offers the most accurate diagnosis and description of the UC. However, the cystoscopy is expensive and invasive, and it is a painful inspection method for patients. Thus, there is a crucial need for noninvasive, objective, and rapid markers that offer adequate sensitivity and specificity for surveillance and diagnosis of the UC.

Exosomes are membranous microvesicles, fusions of late endosomes and cell membranes, released by living cells into surrounding biofluids. The reported diameter of exosomes is between 30 nm and 100 nm. After exocytosis of the exosomes, the exosomes can be reabsorbed into the cytoplasm via a lipid rafts mediated endocytosis, a clathrin-dependent endocytosis and a caveolin-dependent endocytosis. Recent studies reported that the exosomes of cancer cells play an important regulatory role on the process of cancer and concentrations of the exosomes can be used for detecting the cancers and stages. Another report also reports that urinary exosomes from the patients with high-grade bladder cancer can promote UC cells migration and angiogenesis. However, the current methods for validating an existence of the urinary exosome rely on an electron microscopy, a flow cytometry or a Western immunoblotting. These methods are time-consuming and expensive, thus they can not rapidly validate the existence of the urinary exosome.

SUMMARY

According to one aspect of the present disclosure, a method for validating an existence of a urinary exosome includes steps as follows. A sampling step is provided, wherein a urine sample is obtained from a subject. A serially centrifugation step is performed on the urine sample, wherein the serially centrifugation step further includes steps as follows. The urine sample is centrifuged to obtain a first supernatant and a first precipitate. The first precipitate is resuspended with an isolation solution to obtain a first mixture, and the first mixture is centrifuged to obtain a second supernatant and a second precipitate. The first supernatant and the second supernatant are mixed to obtain a second mixture, and the second mixture is centrifuged to obtain a third precipitate. Then an extraction step is provided, wherein the third precipitate is resuspended with an extraction solvent to obtain a third mixture, the third mixture is centrifuged to obtain a fourth supernatant, and the extraction solvent is formic acid and/or acetonitrile. A mass spectrometric analysis step is performed on the fourth supernatant by using a matrix-assisted laser desorption ionization-time of flight mass spectrometry (MALDI-TOF MS), wherein the urinary exosome is existed in the fourth supernatant when at least two polypeptides of a 3367 m/z polypeptide, a 3441 m/z polypeptide, a 3483 m/z polypeptide and a 10884 m/z polypeptide are detected in the fourth supernatant.

According to another aspect of the present disclosure, a non-invasive method for identifying an urothelial cancer includes steps as follows. A sampling step is provided, wherein a urine sample is obtained from a subject. A serially centrifugation step is performed on the urine sample, wherein the serially centrifugation step further includes steps as follows. The urine sample is centrifuged to obtain a first supernatant and a first precipitate. The first precipitate is resuspended with an isolation solution to obtain a first mixture, and the first mixture is centrifuged to obtain a second supernatant and a second precipitate. The first supernatant and the second supernatant are mixed to obtain a second mixture, and the second mixture is centrifuged to obtain a third precipitate. Then an extraction step is provided, wherein the third precipitate is resuspended with an extraction solvent to obtain a third mixture, the third mixture is centrifuged to obtain a fourth supernatant, and the extraction solvent is formic acid and/or acetonitrile. A mass spectrometric analysis step is performed on the fourth supernatant by using a matrix-assisted laser desorption ionization-time of flight mass spectrometry (MALDI-TOF MS) to detect whether the fourth supernatant has a 5593 m/z polypeptide and/or a 5947 m/z polypeptide.

According to yet another aspect of the present disclosure, a method for predicting a recurrence and a progression of an urothelial cancer patient after a treatment includes steps as follows. A sampling step is provided, wherein a urine sample is obtained from a subject. A serially centrifugation step is performed on the urine sample, wherein the serially centrifugation step further includes steps as follows. The urine sample is centrifuged to obtain a first supernatant and a first precipitate. The first precipitate is resuspended with an isolation solution to obtain a first mixture, and the first mixture is centrifuged to obtain a second supernatant and a second precipitate. The first supernatant and the second supernatant are mixed to obtain a second mixture, and the second mixture is centrifuged to obtain a third precipitate. Then an extraction step is provided, wherein the third precipitate is resuspended with an extraction solvent to obtain a third mixture, the third mixture is centrifuged to obtain a fourth supernatant, and the extraction solvent is formic acid and/or acetonitrile. A mass spectrometric analysis step is performed on the fourth supernatant by using a matrix-assisted laser desorption ionization-time of flight mass spectrometry (MALDI-TOF MS), wherein the urothelial cancer patient is determined to have a high recurrence and a high progression after the treatment when a 5947 m/z polypeptide is detected in the fourth supernatant.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

Figure 1:
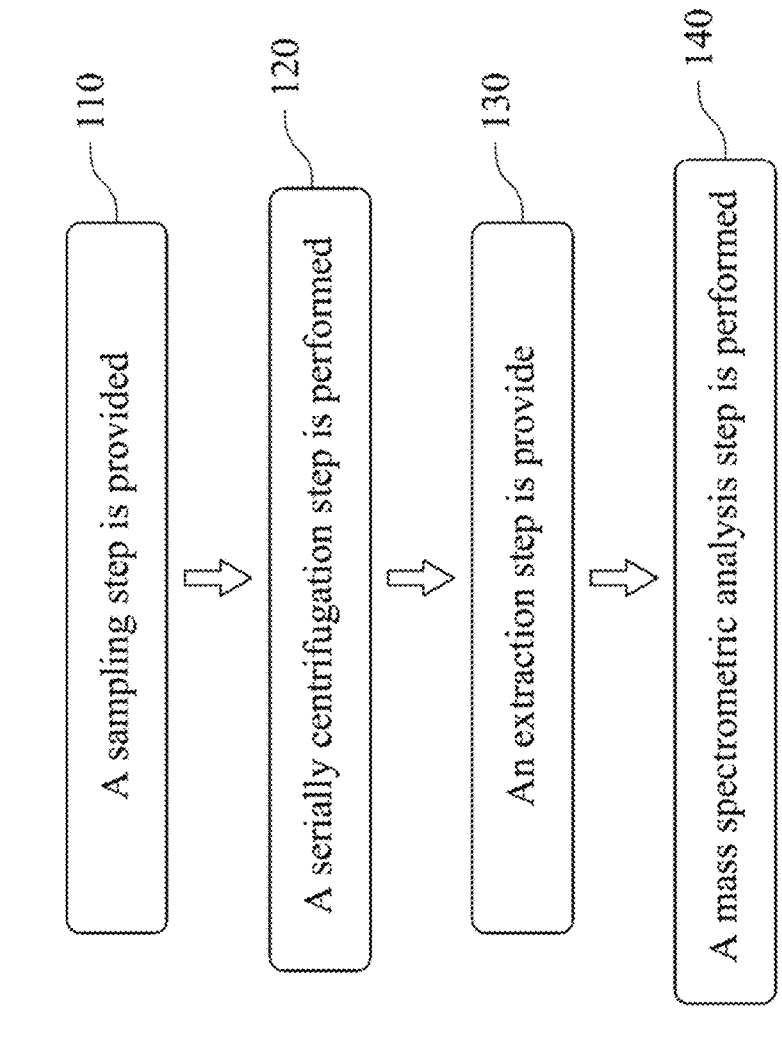
FIG. 1 is a flow diagram showing a method for validating an existence of a urinary exosome according to one embodiment of the present disclosure.

A method for validating an existence of a urinary exosome, a non-invasive method for identifying an urothelial cancer and a method for predicting a recurrence and a progression of an urothelial cancer patient after a treatment are provided. An exosome isolated from a urine sample is extracted by formic acid and/or acetonitrile. Then a mass spectrometric analysis step is performed by using a matrix-assisted laser desorption ionization-time of flight mass spectrometry to detect whether there is a particular peptide therein for validating the existence of the urinary exosome, identifying the urothelial cancer in a subject and predicting the recurrence and the progression of the urothelial cancer patient after the treatment. The following are descriptions of the specific terms used in the specification.

The term "neutrophil defensin" is a highly basic cationic polypeptide that is also referred to as human neutrophil peptide. The neutrophil defensin belongs to a kind of antimicrobial peptides. The neutrophil defensins are abundant in neutrophils, epithelial cells, lining the bronchial tress, genitourinary tract and the urinary exsomes.

The term "S100 calcium-binding protein A9" is also known as MRP14 (migration inhibitory factor-related protein 14) or calgranulin B. It is a calcium and zinc binding protein in the S100 protein family, which is a calcium-binding protein secreted by the neutrophils and other cells and released in inflammation.

The term "α-1 antitrypsin" belongs to a family of serum proteinase inhibitor, which accounts for more than 90% of the total plasma proteases. The α-1 antitrypsin can inhibit a variety of serine endopeptidase, such as neutrophil elastase, trypsin, plasma and thrombin. The main function of the α-1 antitrypsin is to protect cells and organs damaged from proteases and inhibit infections and inflammation for maintaining balance of body environment.

The term "H2B1K (histone H2B)" is one of the most abundantly monoubiquitinated conjugates in nucleus and is involved in transcriptional control of gene expression and DNA damage response. Levels of ubiquitinated H2B are low in advanced cancers including breast, colorectal, lung and parathyroid.

Reference will now be made in detail to the present embodiments of the present disclosure, examples of which are illustrated in the accompanying drawings.

EXAMPLES

I. Subjects

This clinical trial program is approved by China Medical University & Hospital Research Ethics Committee, wherein 119 subjects include 129 urothelial cancer (UC) patients, 17 urinary tract infection (UTI) patients, 25 prostate cancer (PC) patients and 20 healthy subjects.

Table 1 shows clinical features of the subjects, wherein variables of all subjects include age and gender, and the variables of the UC patients further include a tumor location at presentation, a pathologic stage, a pathological grade, a tumor diameter, a number of tumors, surgical methods, a lymphovascular invasion, a lymph node metastasis, a chemotherapy and a surgical margin. The progression is defined as a distant metastasis, a superficial progression to a muscle invasion, or a cancer-related death. The recurrence is defined as new tumor noted after a transurethral resection bladder tumor (TURBT), secondary primaries, the progression, or the distant metastasis. In terms of the age and gender as the variables, there are no significant difference among the UC patients, the UTI patients, the PC patients and the healthy subjects (p value is 0.178 and 0.328 respectively). In the UC patients, 48.8% of patients have pathological stage pTa/Tis/T1, 71.3% of patients have high-grade UC, 79.9% of patients have maximum tumor diameters <3 cm, 62.8% of patients have multiple tumors, 27.7% of patients have lymphovascular invasion, 7.8% of patients have lymph node metastasis, and 5.4% of patients have positive surgical margins.

II. A Method for Validating an Existence of a Urinary Exosome of the Present Disclosure 2.1 Steps of the Method for Validating the Existence of the Urinary Exosome FIG. 1 is a flow diagram showing a method 100 for validating an existence of a urinary exosome according to one embodiment of the present disclosure. The method 100 for validating the existence of the urinary exosome includes a step 110, a step 120, a step 130 and a step 140.

In the step 110, a sampling step is provided. First morning urine samples are obtained from the subjects. For each urine sample (~50 ml), one protease inhibitor cocktail tablet (Roche, Mannheim, Germany) is added. The urine sample is centrifuged at 1,000×g for 10 minutes to remove debris.

TABLE 1

The clinical features of the subjects

| Variable | UC | UTI | PC | Normal | P value |
|---|---|---|---|---|---|
| Total, n | 129 | 17 | 25 | 20 | — |
| Age (yrs) | 67.34 ± 11.35 | 64.41 ± 7.68 | 63.65 ± 8.85 | 69.88 ± 9.96 | 0.178 |
| Gender, Male (%) | 85 (65.9%) | 7 (41.2%) | 25 (100%) | 11 (55%) | 0.328 |
| Tumor location at presentation, n (%) | | | | | |
| Bladder | 70 (54.3%) | — | — | — | — |
| Ureter or Renal pelvis | 59 (45.7%) | — | — | — | — |
| Pathologic stage, n (%) | | | | | |
| pTa/Tis/T1 | 63 (48.8%) | — | — | — | — |
| pT2 | 30 (23.3%) | — | — | — | — |
| pT3/T4 | 36 (27.9%) | — | — | — | — |
| Pathological grade, n (%) | | | | | |
| Low | 37 (28.7%) | — | — | — | — |
| High | 92 (71.3%) | — | — | — | — |
| Tumor diameter, n (%) | | | | | |
| <1 cm | 29 (22.5%) | — | — | — | — |
| 1-3 cm | 74 (57.4%) | — | — | — | — |
| ≥3 cm | 26 (20.1%) | — | — | — | — |
| Number of tumors, n (%) | | | | | |
| Single | 48 (37.2%) | — | — | — | — |
| Multiple | 81 (62.8%) | — | — | — | — |
| Surgical Methods | | | | | |
| TURBT | 68 (52.7%) | — | — | — | — |
| Cystectomy | 15 (11.6%) | — | — | — | — |
| Nephrouretectomy | 46 (35.7%) | — | — | — | — |
| Lymphovascular invasion, n (%) | | | | | |
| Total | 65 | — | — | — | — |
| Positive | 18 (27.7%) | — | — | — | — |
| Negative | 47 (72.3%) | — | — | — | — |
| Lymph node metastasis | | | | | |
| Positive | 10 (7.8%) | — | — | — | — |
| Negative | 119 (92.2%) | — | — | — | — |
| Chemotherapy | | | | | |
| Intravesical | 69 (53.5%) | — | — | — | — |
| Adjuvant | 32 (24.8%) | — | — | — | — |
| No | 28 (21.7%) | — | — | — | — |
| Surgical margin, n (%) | | | | | |
| Positive | 7 (5.4%) | — | — | — | — |
| Negative | 122 (94.6%) | — | — | — | — |

Then the urine sample is stored at −80° C. until subsequent serially centrifugation step or directly performed the serially centrifugation step.

In the step 120, a serially centrifugation step is performed on the urine sample, wherein the serially centrifugation step further includes steps as follows. Aforementioned urine sample is centrifuged at 17,000×g for 10 minutes at 4° C. to obtain a first supernatant and a first precipitate. The first supernatant is collected in a new tube, and the first precipitate is resuspended with an isolation solution (10 mm triethanolamine/250 mm sucrose, pH 7.6, and 0.5 mm PMSF) before adding 200 mg/ml dithiotheritol to obtain a first mixture. The first mixture is incubated at 95° C. for 2 minutes, and then centrifuged at 17,000×g for 30 minutes at 4° C. to obtain a second supernatant and a second precipitate. The first supernatant and the second supernatant are mixed to obtain a second mixture, and the second mixture is centrifuged at 200,000×g for 1 hour at 4° C. to obtain a third precipitate.

In the step 130, an extraction step is provided. The third precipitate is resuspended with an extraction solvent to obtain a third mixture, wherein the extraction solvent is formic acid and/or acetonitrile. Further, the extraction solvent is the formic acid at a weight percentage in a range from 50% to 98% or a mixture of the formic acid at the weight percentage in the range from 25% to 50% and 50 weight percentage of the acetonitrile. Then the third mixture is centrifuged at 10,000×g for 15 minutes at 4° C. to remove insoluble sediment and obtain a fourth supernatant.

In the step 140, a mass spectrometric analysis step is performed on the fourth supernatant by using a matrix-assisted laser desorption ionization-time of flight mass spectrometry (MALDI-TOF MS), wherein the urinary exosome is existed in the fourth supernatant when at least two polypeptides of a 3367 m/z polypeptide, a 3441 m/z polypeptide, a 3483 m/z polypeptide and a 10884 m/z polypeptide are detected in the fourth supernatant. The 3367 m/z polypeptide has amino acid sequence of SEQ ID NO:1, the 3441 m/z polypeptide has amino acid sequence of SEQ ID NO:2, the 3483 m/z polypeptide has amino acid sequence of SEQ ID NO:3, and the 10884 m/z polypeptide has amino acid sequence of SEQ ID NO:4.

2.2 Confirmation of the Urinary Exosome

To confirm the urinary exosome can be isolated by the step 110 and the step 120, expressions of biomarkers of the urinary exosome in the third precipitate treated with the step 110 and the step 120 are analyzed by a Western immunoblotting, and morphology of the urinary exosome is observed by a transmission electron microscope.

The steps of the Western immunoblotting are as follows. The third precipitate is lysed by RIPA lysis buffer (10 mM Tris-HCl, 1 mM EDTA, 1 mM EGTA, 50 mM NaCl, 50 mM NaF, 20 mM $Na_4P_2O_7$, 1 mM $Na_3VO_4$, and 1% Triton X-100). The lysis is transferred to a microcentrifuge tube, and then centrifuged at 12,000×g for 10 minutes to a supernatant. The protein concentration is determined by Bradford protein quantification. 20 μg proteins are solubilized in Laemmli sample buffer (1.5% SDS, 6% glycerol, and 10 mM Tris-HCl (pH 6.8)), and then boiled at 100° C. for 10 minutes. The proteins with different physical properties are separated by a one-dimensional sodium dodecyl sulfate-polyacrylamide gel electrophoresis (1D SDS-PAGE) and transferred electrophoretically onto polyvinylidene fluoride (PVDF) membranes. After blocking the PVDF membranes with 5% nonfat milk at room temperature for 1 hour, the PVDF membranes are probed overnight at 4° C. with primary monoclonal antibodies to TSG101 (1:500) (Thermo Scientific), Alix (1:200) (chemicon) and actin (1:1000) (Rockland). The TSG101 and the Alix are the biomarkers of the exosome, and the actin is an internal control. Thereafter, the PVDF membranes are probed with peroxidase-conjugated anti-rabbit or anti-mouse IgG (1:10,000) for 1 hour at room temperature. Immunoreactivity is detected by enhanced chemiluminescence.

Figure 2:
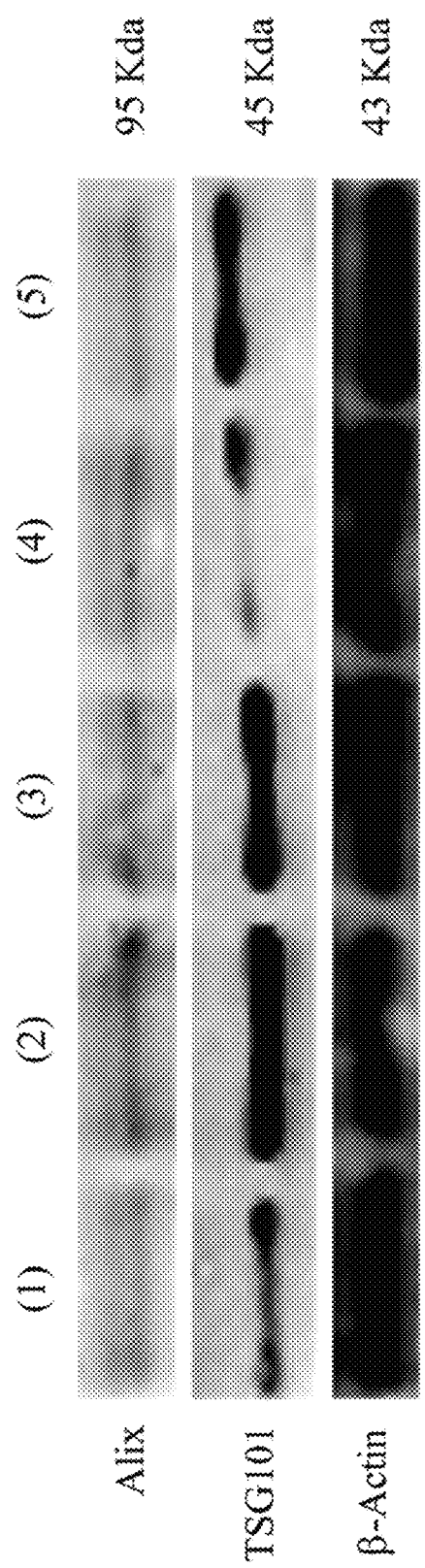
FIG. 2 is analytical results of a Western immunoblotting to detect biomarkers of a urinary exosome of a subject.

FIG. 2 is analytical results of the Western immunoblotting to detect biomarkers of the urinary exosome of the subject. The (1) to (5) represent the urine samples obtained from different groups of the subjects, wherein (1) is the group of the patients with low-grade urothelial cancer, (2) is the group of the patients with high-grade urothelial cancer, (3) is the group of the patients with the prostate cancer, (4) is the group of the patients with the urinary tract infection, and (5) is the group of the healthy subjects. In FIG. 2, the third precipitate isolated from different groups of the subjects can be detected TSG101 expressions and Alix expressions. It indicates that the urinary exosome can be isolated by the step 110 and the step 120.

The third precipitate is further resuspended in 2.5% glutaraldehyde and applied to Formvar-coated carbon-stabilized copper grids. The grids are dried at room temperature, washed twice with PBS, and then stained with 2% (w/v) uranyl acetate for 10 minutes. The grid is examined with a JOEL 200CX transmission electron microscope.

Figure 3:
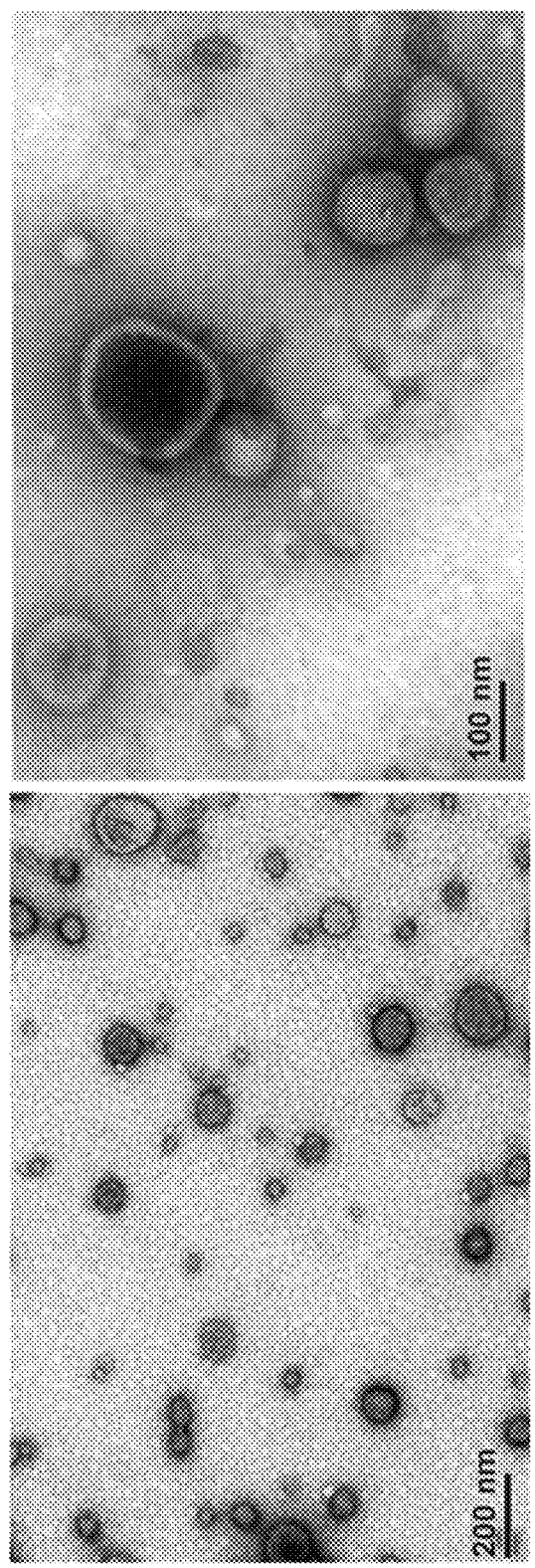
FIG. 3 is a set of micrographs of a transmission electron microscope of the urinary exosome of the subject.

FIG. 3 is a set of micrographs of the transmission electron microscope of the urinary exosome of the subject. Under the transmission electron microscope, round-shaped membranous vesicles with ~50 nm to 100 nm diameters are clearly observed in the third precipitate, which are consistent with the morphology of the exosome. It indicates that the urinary exosome can be isolated by the step 110 and the step 120 indeed.

2.3 Comparison of the Results of the Urinary Exosome Extracted by Different Extraction Solvents To test the best extraction conditions in the step 130, the third precipitate is extracted by fourteen different extraction conditions respectively in this example. The extraction condition is (1) $ddH_2O$ as the extraction solvent, (2) 25 weight percentage of the acetonitrile as the extraction solvent, (3) 50 weight percentage of the acetonitrile as the extraction solvent, (4) 75 weight percentage of the acetonitrile as the extraction solvent, (5) 25 weight percentage of the formic acid as the extraction solvent, (6) 50 weight percentage of the formic acid as the extraction solvent, (7) 75 weight percentage of the formic acid as the extraction solvent, (8) 98 weight percentage of the formic acid as the extraction solvent, (9) the mixture of 25 weight percentage of the formic acid with 50 weight percentage of the acetonitrile as the extraction solvent, (10) the mixture of 35 weight percentage of the formic acid with 50 weight percentage of the acetonitrile as the extraction solvent, (11) the mixture of 45 weight percentage of the formic acid with 50 weight percentage of the acetonitrile as the extraction solvent, (12) the mixture of 50 weight percentage of the formic acid with 50 weight percentage of the acetonitrile as the extraction solvent, (13) the RIPA lysis buffer as the extraction solvent with a sonication, and (14) sonication, respectively. Aforementioned extraction solvent is respectively added into the third precipitate to obtain the third mixture, and the third mixture is centrifuged at 10,000×g for 15 minutes at 4° C. to remove the insoluble sediment and obtain the fourth supernatant. Each extraction condition is repeated with eight technical replicates.

The concentration of total proteins in the fourth supernatant obtained from aforementioned fourteen different extraction conditions is determined by the Bradford protein quantification respectively. The difference among the eight technical replicates at each extraction condition is compared by statistical software. The extracted proteins are further analyzed by the 1D SDS-PAGE and a silver stain, wherein 12% SDS-polyacrylamide gel is used in the 1D SDS-PAGE. The electrophoresis is performed on a power supply set at 75 V/gel for the stacking gel and 110 V/gel for the resolving gel. All gels are placed in fixing solution (methanol:acetic acid:deionized water=40:10:50) for 1 hour, then washed twice in ddH$_2$O for 10 minutes. The gels are stained with silver stain, and then analyzed bands of the gels.

Figure 4A:
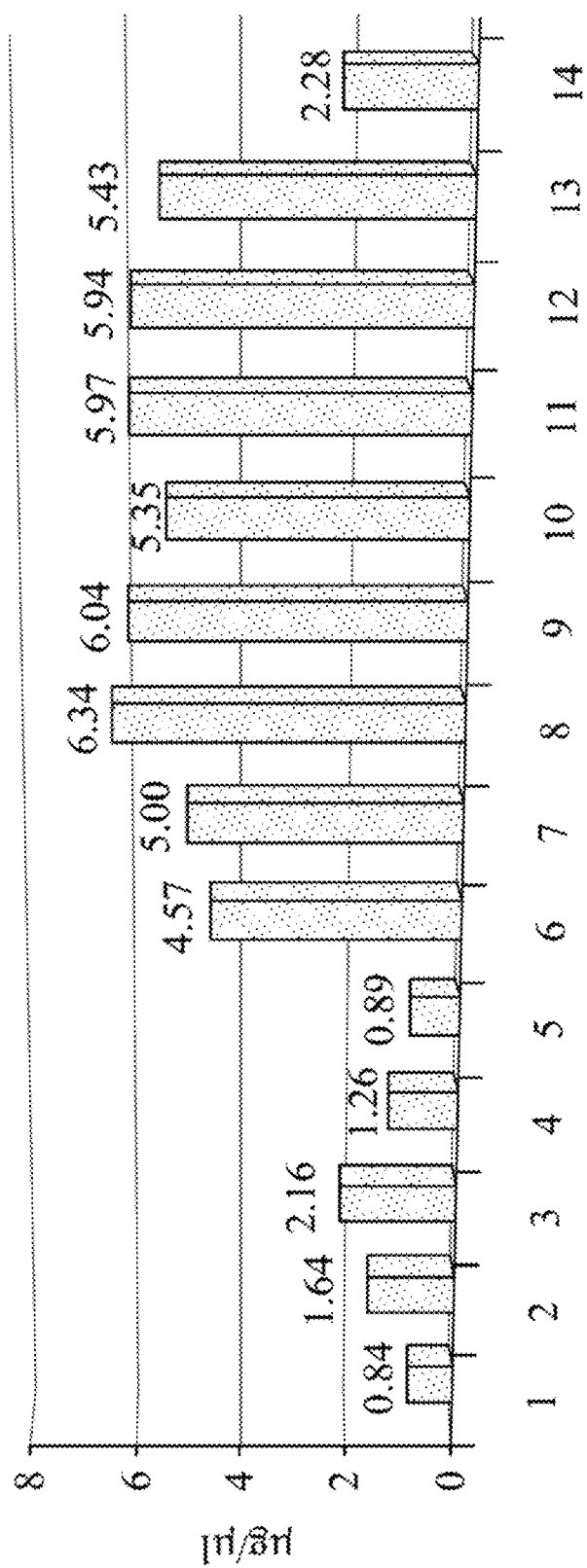
FIG. 4A is a protein quantitative results according to one embodiment of the present disclosure.

FIG. 4A is the protein quantitative results according to one embodiment of the present disclosure. In FIG. 4A, there is no statistical difference among the eight technical replicates at each extraction condition (p value is 0.99, determined by ANOVA test). High percentage (50% to 98%) of the formic acid or the mixture of 25% to 50% of the formic acid with 50% of the acetonitrile as the extraction solvent (extraction conditions (6)-(13)) yields similar protein concentration. Furthermore, the protein concentrations of the fourth supernatant obtained from the extraction conditions (6)-(13) are higher than that obtained from the extraction conditions (1)-(5) and (14).

Figure 4B:
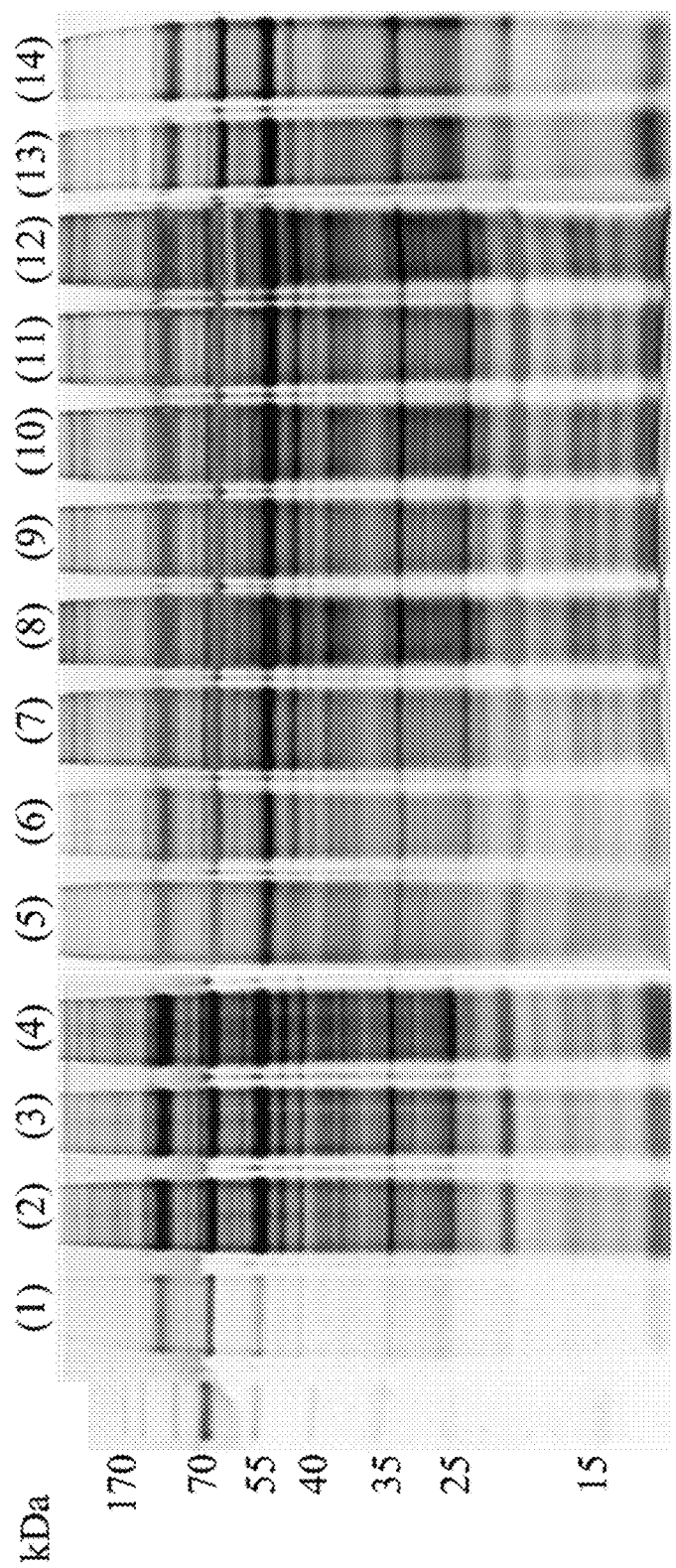
FIG. 4B is analytical result of a sliver stain according to one embodiment of the present disclosure.

FIG. 4B is analytical result of sliver stain according to one embodiment of the present disclosure. In FIG. 4B, the extraction conditions (6)-(13) produce more prominent bands at both high molecular weights and low molecular weights via the 1D SDS-PAGE separating the proteins with different physical properties. It indicates that the proteins and the protein concentration of the exosome extracted by the formic acid and/or the acetonitrile in the present disclosure is similar to that extracted by the RIPA lysis buffer (the conventional method).

2.4 Biomarkers for Validating the Existence of the Urinary Exosome

The fourth supernatant obtained from aforementioned fourteen different extraction conditions is further performed the mass spectrometric analysis step by the MALDI-TOF MS respectively. The analyte solution is mixed with saturated sinapinic acid (SA) solution (30:70 acetonitrile/0.1% trifluoroacetic acid) at volume ratios of 1:1 or 1:5. 1 μL of the analyte/SA solution is placed on the MALDI-TOF target. After analyte/SA co-crystallization, the sample plate is analyzed by MALDI-TOF (Ultraflex III TOF/TOF; Bruker Daltonics). The MALDI-TOF is operated in linear positive ion mode with 25-kV accelerating voltage at a laser frequency of 50 Hz with a mass range from 1000 to 23,000 Da. Peptide/protein calibrations are carried out using a peptide/protein calibration standard kit (Bruker Daltonics). MALDI-TOF mass spectra are processed using flexAnalysis 3.0 software (Bruker Daltonics).

Figure 5A:
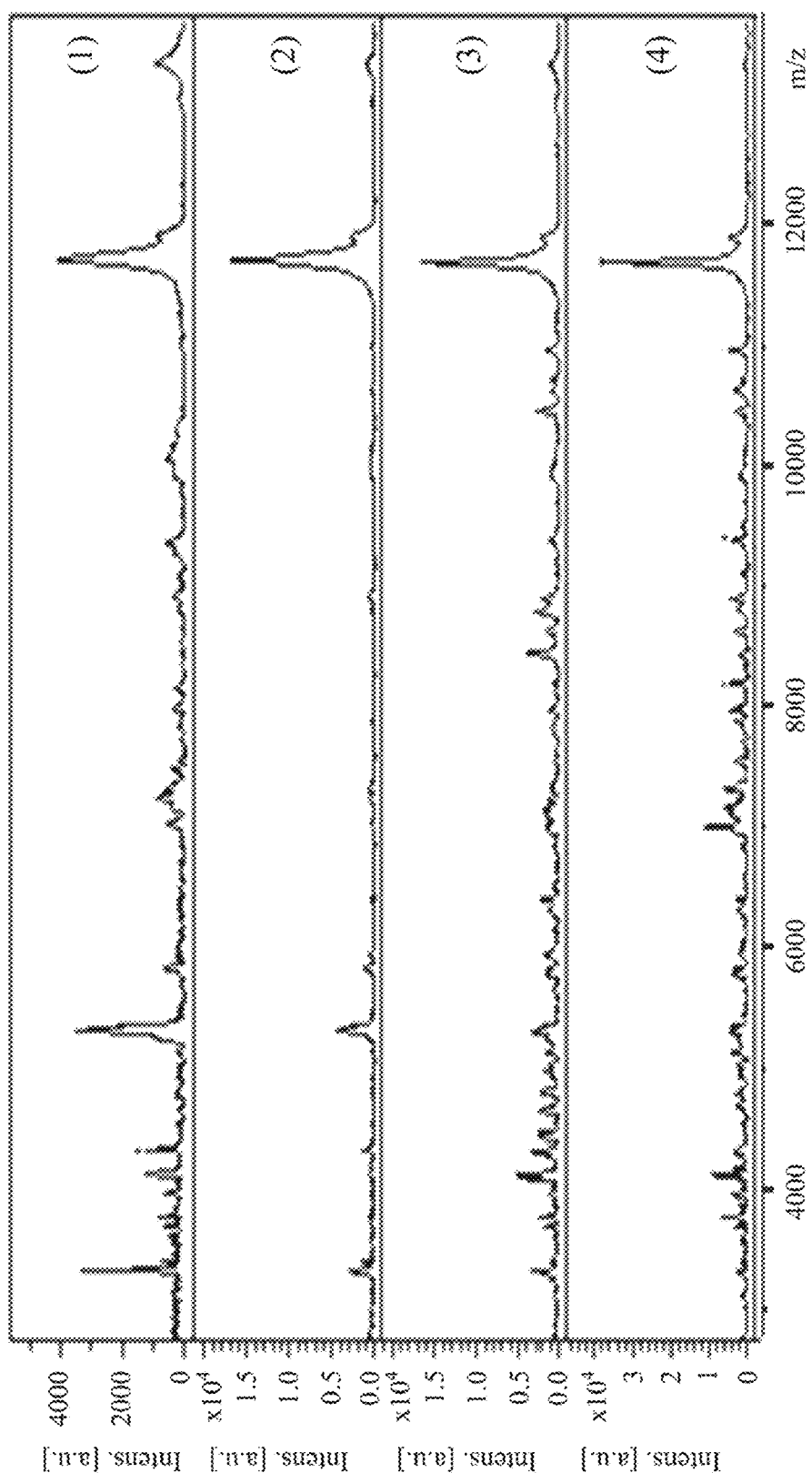
FIGS. 5A to 5D are MALDI-TOF mass spectra according to one embodiment of the present disclosure.
Figure 5B:
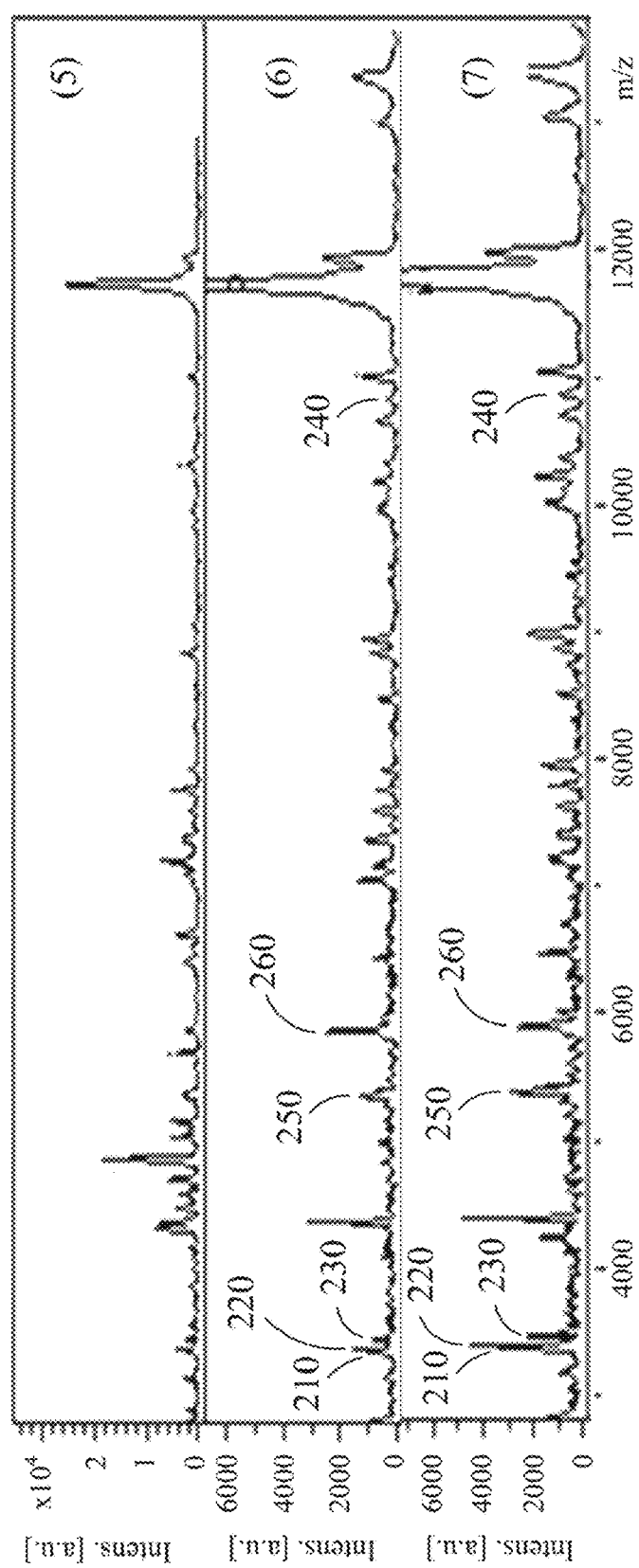
Figure 5C:
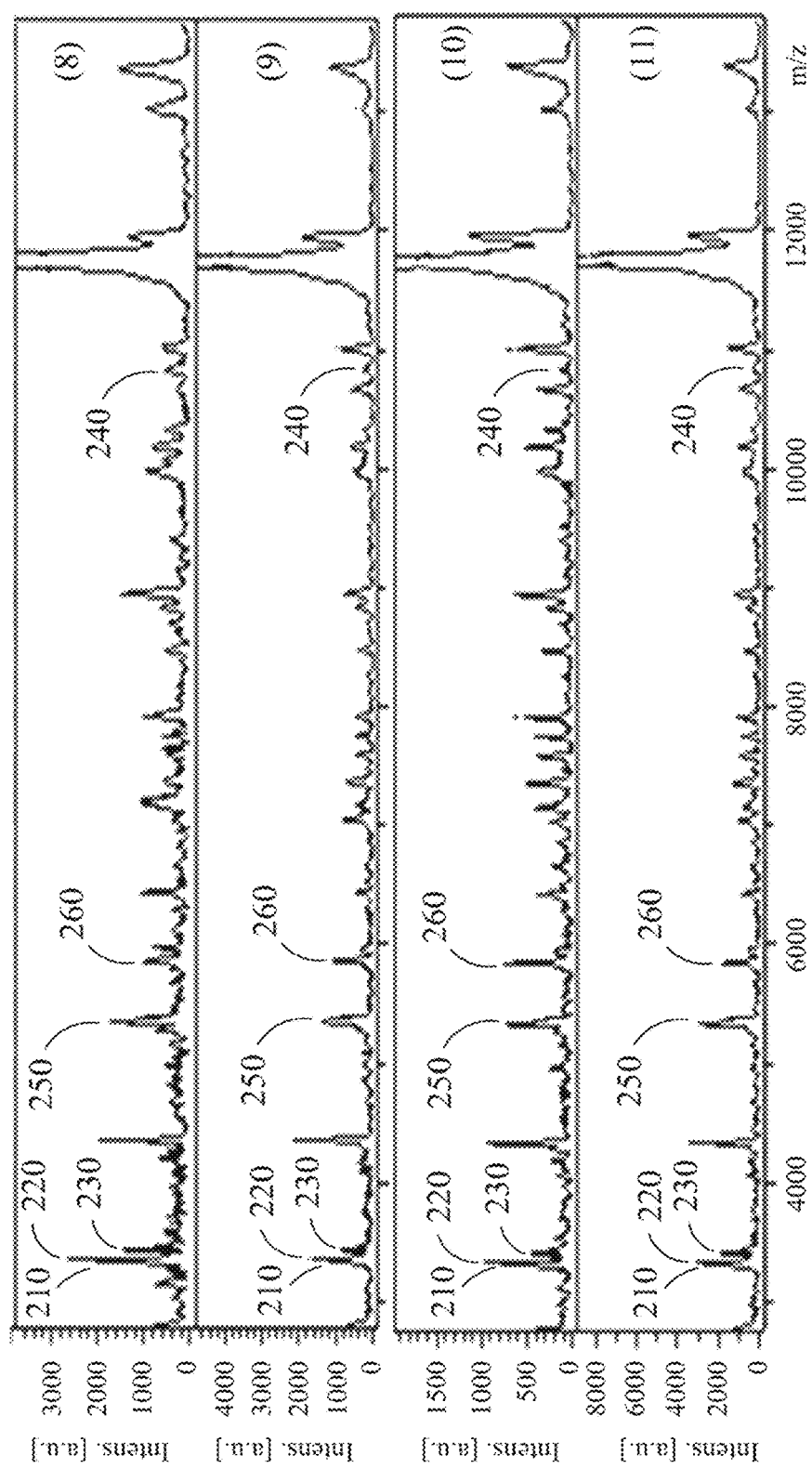
Figure 5D:
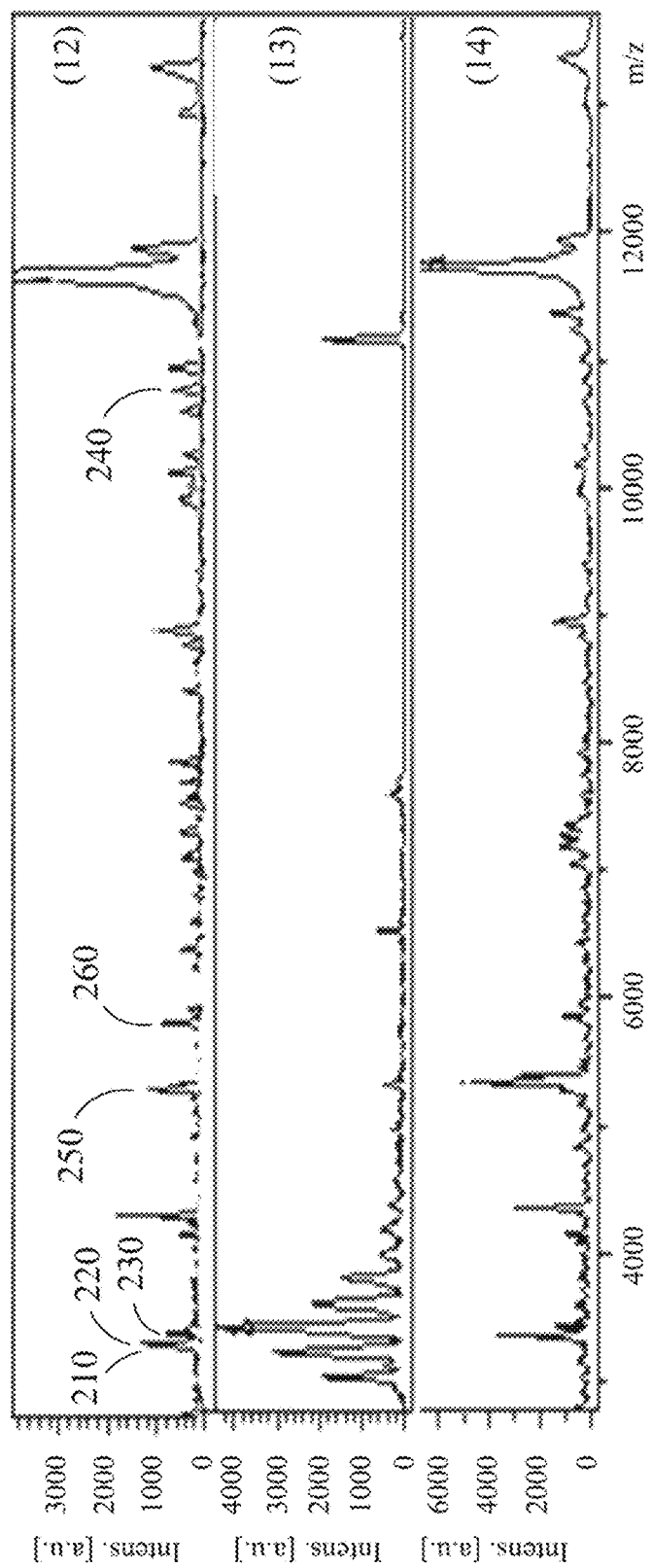

FIGS. 5A to 5D are the MALDI-TOF mass spectra according to one embodiment of the present disclosure, wherein FIG. 5A are the MALDI-TOF mass spectra of the fourth supernatant obtained from extraction conditions (1)-(4), FIG. 5B are the MALDI-TOF mass spectra of the fourth supernatant obtained from extraction conditions (5)-(7), FIG. 5C are the MALDI-TOF mass spectra of the fourth supernatant obtained from extraction conditions (8)-(11), and FIG. 5D are the MALDI-TOF mass spectra of the fourth supernatant obtained from extraction conditions (12)-(14). In FIGS. 5A to 5D, the fourth supernatant obtained from the extraction conditions (6)-(12) has similar MALDI-TOF mass spectrum producing particular peaks at m/z 3367, m/z 3441, m/z 3483, m/z 5593, m/z 5947 and m/z 10884, which represents the 3367 m/z polypeptide 210, the 3441 m/z polypeptide 220, the 3483 m/z polypeptide 230, the 5593 m/z polypeptide 250, the 5947 m/z polypeptide 260 and the 10884 m/z polypeptide 240. However, because the extraction condition (13) uses the RIPA lysis buffer containing detergent and salts, the MALDI-TOF signals are significantly impaired despite performing sample purification prior to MALDI-TOF analysis. Therefore, the MALDI-TOF mass spectrum of the fourth supernatant obtained from extraction condition (13) is significant different from the MALDI-TOF mass spectra of the fourth supernatant obtained from extraction conditions (6)-(12). 75% of the formic acid is selected as the extraction solvent for subsequent examples.

To confirm that whether there are same particular polypeptides or different particular polypeptides in different groups of the subjects, the MALDI-TOF mass spectra of the fourth supernatant extracted from the UC patients, the UTI patients, the PC patients and the healthy subjects are compared by a two-dimensional (2-D) pseudo gel.

Figure 6:
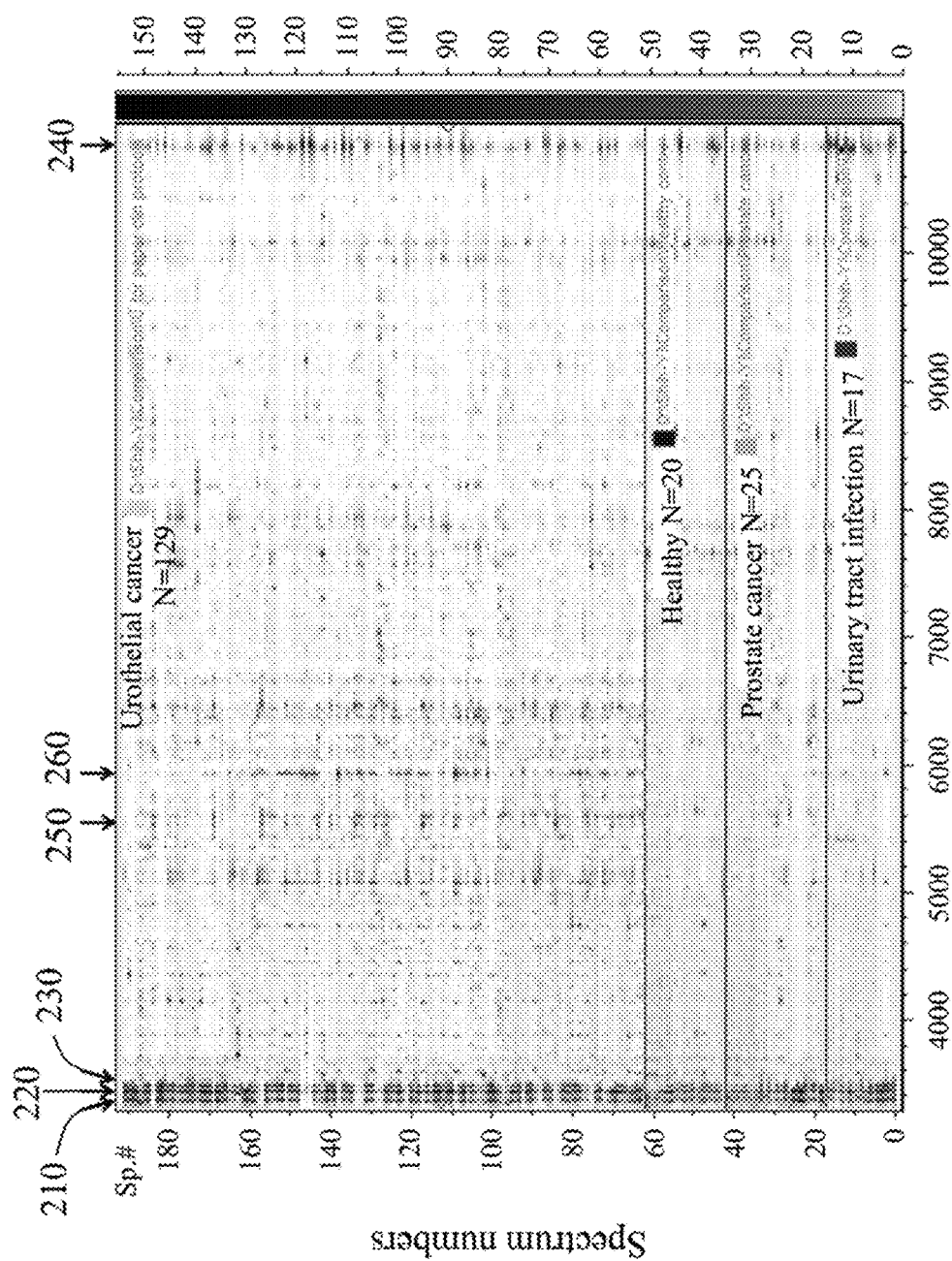
FIG. 6 is an analytical result of a 2-D pseudo gel according to one embodiment of the present disclosure.

FIG. 6 is an analytical result of the 2-D pseudo gel according to one embodiment of the present disclosure. In FIG. 6, the 3367 m/z polypeptide 210, the 3441 m/z polypeptide 220, the 3483 m/z polypeptide 230 and the 10884 m/z polypeptide 240 are consistently detected in the exosomes from the UC patients and the non-UC subjects. Therefore, the 3367 m/z polypeptide 210, the 3441 m/z polypeptide 220, the 3483 m/z polypeptide 230 and the 10884 m/z polypeptide 240 can act as the biomarkers for identifying the urinary exosome. Furthermore, when at least two polypeptides of the 3367 m/z polypeptide 210, the 3441 m/z polypeptide 220, the 3483 m/z polypeptide 230 and the 10884 m/z polypeptide 240 are detected, the urinary exosome is existed.

The sequence of the 3367 m/z polypeptide 210, the 3441 m/z polypeptide 220, the 3483 m/z polypeptide 230 and the 10884 m/z polypeptide 240 are further identified in this example. The concentration of the total proteins in the fourth supernatant is determined by the Bradford protein quantification. The samples of the different groups are taken at fixed protein amount. For higher separation resolution, electrophoresis on 4% to 12% Bis-Tris NuPAGE® gels (Invitrogen) is performed to purify and separate the 3367 m/z polypeptide 210, the 3441 m/z polypeptide 220 and the 3483 m/z polypeptide 230. The electrophoresis is performed at 75 V/gel for the stacking gel and 110 V/gel for the resolving gel. After separation, the gel is stained with Coomassie Brilliant Blue G250 and destained by ddH$_2$O. Peptide bands ~3000 Da are excised and extracted with 50% acetonitrile 10.1% formic acid. The extracted peptides are analyzed by the MALDI-TOF MS to confirm the presence of the 3367 m/z polypeptide 210, the 3441 m/z polypeptide 220 and the 3483 m/z polypeptide 230, and then identified by a nanoLC-MS/MS analysis. The 3367 m/z polypeptide 210 is identified as a peptide fragment of the neutrophil defensin with the sequence referenced as SEQ ID NO: 1 (monoisotopic mass: m/z 3365.7 Da; most abundant mass: m/z 3367.7 Da). The 3441 m/z polypeptide 220 is identified as the peptide fragment of the neutrophil defensin with the sequence referenced as SEQ ID NO: 2 (monoisotopic mass: m/z 3439.9 Da; most abundant mass: m/z 3440.9 Da). The 3483 m/z polypeptide 230 is identified as the peptide fragment of the neutrophil defensin with the sequence referenced as SEQ ID NO: 3 (monoisotopic mass: m/z 3481.8 Da; most abundant mass: m/z 3482.8 Da). The 10884 m/z polypeptide 240 is purified by a liquid chromatography (LC), digested with trypsin, and analyzed by the nano-LC MS/MS. The 10884 m/z polypeptide 240 is identified as a large peptide fragment of the S100 A9 with the sequence referenced as SEQ ID NO: 4 (monoisotopic mass: m/z 10878.428 Da; most abundant mass: m/z 10884.443 Da).

Figure 7:
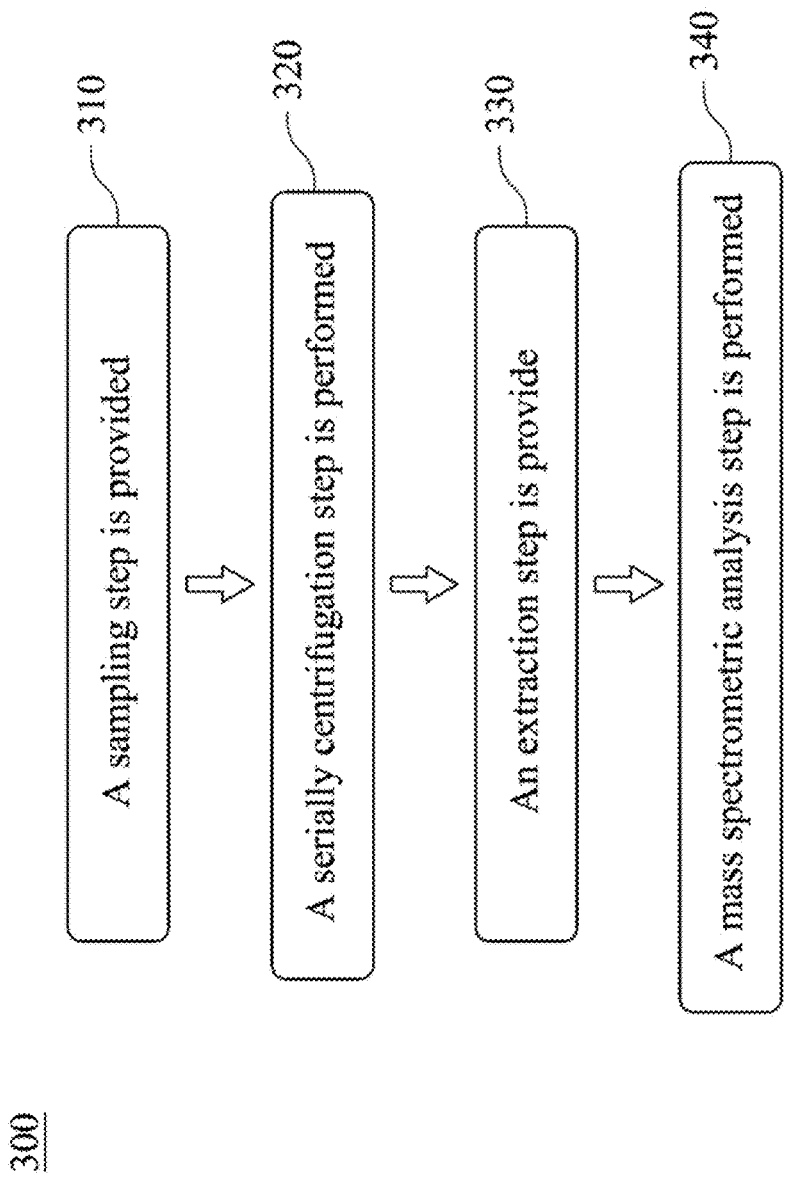
FIG. 7 is a flow diagram showing a non-invasive method for identifying an urothelial cancer according to another embodiment of the present disclosure.

III. A Method for Non-Invasive Method for Identifying an Urothelial Cancer of the Present Disclosure FIG. 7 is a flow diagram showing a non-invasive method 300 for identifying an urothelial cancer according to another embodiment of the present disclosure. The non-invasive method 300 for identifying the urothelial cancer includes a step 310, a step 320, a step 330 and a step 340.

In the step 310, the sampling step is provided. First morning urine samples are obtained from the subjects. For each urine sample (~50 ml), one protease inhibitor cocktail tablet (Roche, Mannheim, Germany) is added. The urine sample is centrifuged at 1,000×g for 10 minutes to remove debris. Then the urine sample is stored at −80° C. until subsequent serially centrifugation step or directly performed the serially centrifugation step.

In the step 320, the serially centrifugation step is performed on the urine sample, wherein the serially centrifugation step further includes steps as follows. The urine sample is centrifuged at 17,000×g for 10 minutes at 4° C. to obtain the first supernatant and the first precipitate. The first supernatant is collected in new tube, and the first precipitate is resuspended with the isolation solution (10 mm triethanolamine/250 mm sucrose, pH 7.6, 0.5 mm PMSF) before adding 200 mg/ml dithiotheritol to obtain the first mixture. The first mixture is incubated at 95° C. for 2 minutes, and then centrifuged at 17,000×g for 30 minutes at 4° C. to obtain the second supernatant and the second precipitate. The first supernatant and the second supernatant are mixed to obtain the second mixture, and the second mixture is centrifuged at 200,000×g for 1 hour at 4° C. to obtain the third precipitate.

In the step 330, the extraction step is provided. The third precipitate is resuspended with the extraction solvent to obtain the third mixture, wherein the extraction solvent is formic acid and/or acetonitrile. Further, the extraction solvent is the formic acid at the weight percentage in the range from 50% to 98% or the mixture of the formic acid at the weight percentage in the range from 25% to 50% with 50 weight percentage of the acetonitrile. Then the third mixture is centrifuged at 10,000×g for 15 minutes at 4° C. to remove the insoluble sediment and obtain the fourth supernatant.

In the step 340, the mass spectrometric analysis step is performed on the fourth supernatant by using the MALDI-TOF MS to detect whether the fourth supernatant has a 5593 m/z polypeptide and/or a 5947 m/z polypeptide 260.

The 5593 m/z polypeptide has amino acid sequence of SEQ ID NO:5, and the 5947 m/z polypeptide 260 has amino acid sequence of SEQ ID NO:6.

3.1 the Biomarkers for Detecting the Urothelial Cancer

Referring back to FIG. 6, which is analytical result of the 2-D pseudo gel according to one embodiment of the present disclosure. The 5593 m/z polypeptide 250 and the 5947 m/z polypeptide 260 are specifically detected in the UC patients compared to the non-UC subjects (the UTI patients, the PC patients and the healthy subjects). Therefore, the 5593 m/z polypeptide 250 and the 5947 m/z polypeptide 260 can act as the biomarkers for identifying the urothelial cancer. The sensitivity and specificity of the 5593 m/z polypeptide 250 alone for detecting the urothelial cancer are 50.4% and 96.9%, respectively, with an AUC (the area under ROC curve) analyzed by ClinPro Tools 3.0 software (Bruker Daltonics) of 0.736. The sensitivity and specificity of the 5947 m/z polypeptide 260 alone for detecting the urothelial cancer are 62.0% and 92.3%, respectively, with the AUC of 0.772. The sensitivity and specificity of the 5593 m/z polypeptide 250 and the 5947 m/z polypeptide 260 combined for detecting the urothelial cancer are 62.70% and 87.59%, respectively, with the AUC of 0.87. Therefore, the 5593 m/z polypeptide 250 and the 5947 m/z polypeptide 260 not only can be used alone as the biomarker for detecting the urothelial cancer but also can be combined used for detecting the urothelial cancer.

The 5593 m/z polypeptide 250 and the 5947 m/z polypeptide 260 are further purified by the LC, digested with trypsin, and analyzed by the nano-LC MS/MS. The 5593 m/z polypeptide 250 is identified as the fragment peptide of α-1-antitrypsin with the sequence referenced as SEQ ID NO: 5 (monoisotopic mass: m/z 5590.089 Da; most abundant mass: m/z 5593.098 Da). The 5947 m/z polypeptide 260 is identified as the fragment peptide of the H2B1K with the sequence referenced as SEQ ID NO: 6 (monoisotopic mass: m/z 5944.107 Da; most abundant mass: m/z 5947.115 Da).

3.2 Protein Expression Levels of Biomarkers of the Urothelial Cancer Detected by an Immunohistochemical Staining To confirm that the α-1 antitrypsin and the H2B1 K can indeed be used as the biomarkers for detecting the urothelial cancer, the immunohistochemical staining is further performed in this example. Tissue speciments of the immunohistochemical staining are obtained from 122 UC patients and 26 healthy subjects.

The steps of the immunohistochemical staining are as follows. The tissue speciments are initially formalin fixed and paraffine embedded. All immunohistochemical staining is carried out on a Leica Bond-Max autostainer (Leica Microsystems) according to the manufacturer's protocol. Antigen retrieval is carried out at pH 8 with Epitope Retrieval 2 solution (Leica Microsystems) for 20 minutes at 100° C. The tissue speciments are then incubated for 15 hours at room temperature with the primary antibodies at the following dilutions: rabbit polyclonal anti-trypsin (1:1600; Novocastra) and rabbit polyclonal H2B1K (1:400; NOVUS). The tissue speciments are conjugated with DAB secondary antibody to detect staining results. After the detection, the tissue speciments are then counterstained by hematoxylin.

In the immunohistochemical staining, the biomarker expression level is analyzed by estimating a staining intensity of the biomarker of the urothelial carcinoma in 25 high power fields (magnification 400×), and it is classified as 0, 1, 2, and 3. A pathologist analyzes the immunohistochemical stained tissue sections without knowing the diagnostic results during the histopathological diagnosis. Criteria of the classification are as follows: 0 represents that no cells are stained with color, 1 represents that the cells are stained with weak intensity of color on intact cell, 2 represents that the cells are stained with moderate intensity of color on intact cell, and 3 represents that the cells are stained with strong intensity of color on intact cell. The stained cell number is estimated as a percentage (stained cell number/total cell number×100%), and a IHC score in the immunohistochemical staining is calculated according to the following formula I:

IHC score=Σ(i×Pi)  formula I, wherein i represents the staining intensity of the biomarker (0, 1, 2, or 3), Pi represents the percentage of the stained cells (varied from 0% to 100%), and the IHC score ranges from 0 to 300.

Figure 8:
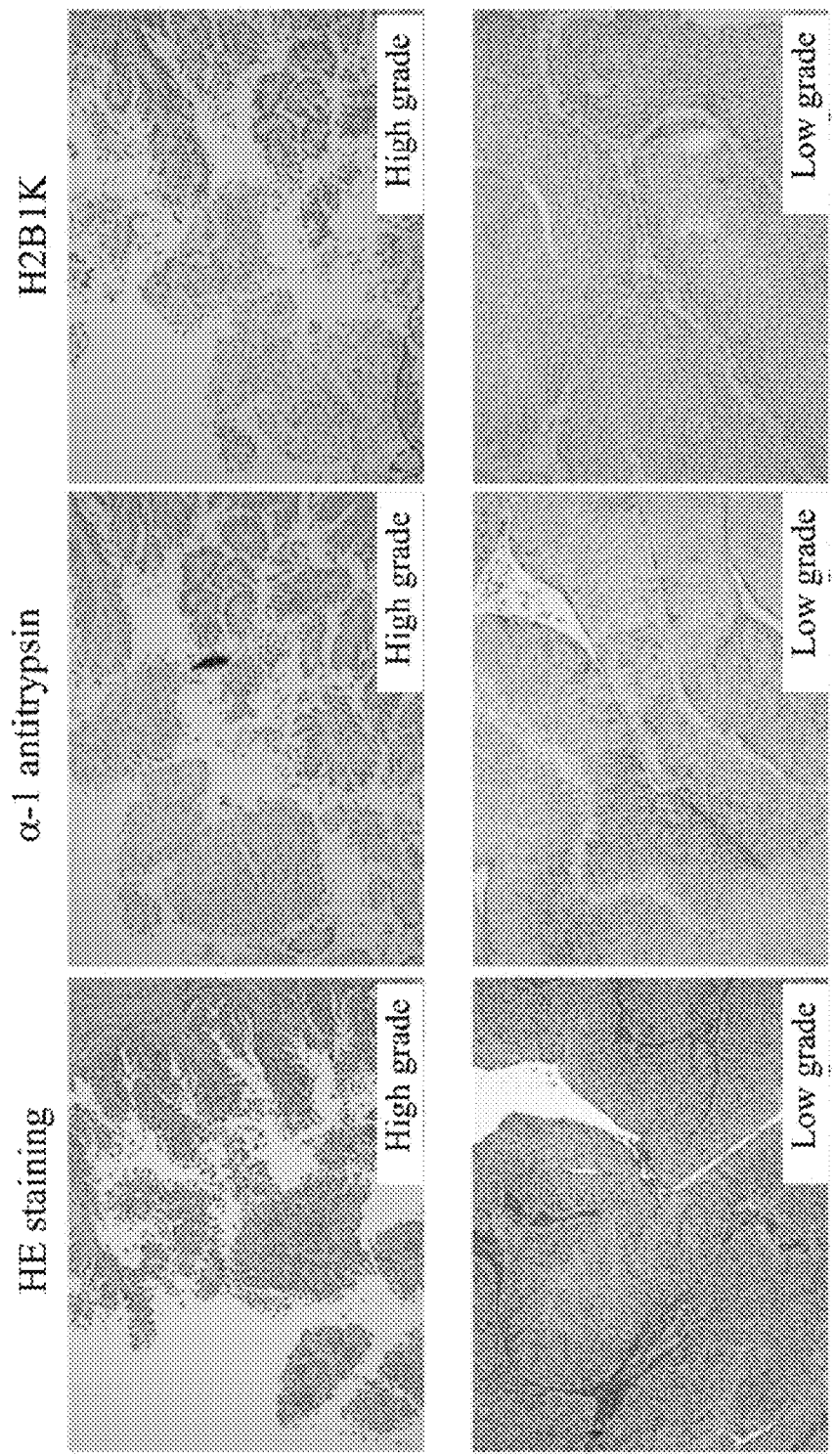
FIG. 8 is a set of micrographs of an immunohistochemical staining.

FIG. 8 is a set of micrographs of the immunohistochemical staining, which includes hematoxylin and eosin staining (HE staining) results in high-grade and low-grade UC tissue specimens and the IHC staining results of the α-1 antitrypsin and the H2B1K in the high-grade and low-grade UC tissue specimens. In FIG. 8, the α-1 antitrypsin is cytoplasmic staining, while the H2B1 K is nuclear staining. In both high-grade and low-grade UC tissue specimens, the staining intensity of the α-1 antitrypsin and the H2B1K in the UC tissue specimen is stronger than neighboring normal uroepithelium.

When comparing the IHC staining results of the UC tissue specimen with that of the non-UC tissue specimen, the sensitivity/specificity of the α-1 antitrypsin and the H2B1 K expression in the UC tissues specimen are 35.2%/96.2%, and 30.8%/96.7%, respectively.

Figure 9A:
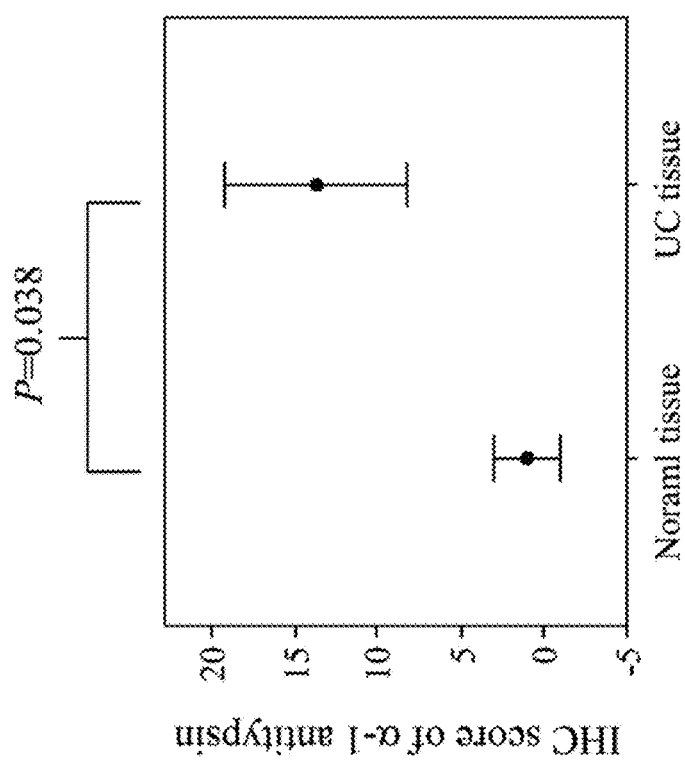
FIG. 9A is a quantification of an IHC score of α-1 antitrypsin expressions in non-UC tissue specimens and UC tissues specimens detected by the immunohistochemical staining.
Figure 9B:
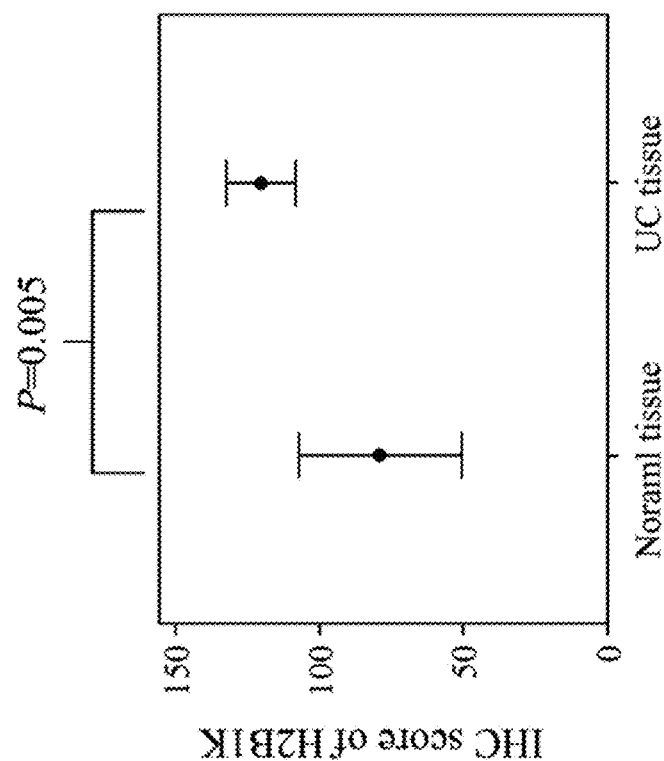
FIG. 9B is the quantification of the IHC score of H2B1K expressions in the non-UC tissue specimens and the UC tissues specimens detected by the immunohistochemical staining.
Figure 10B:
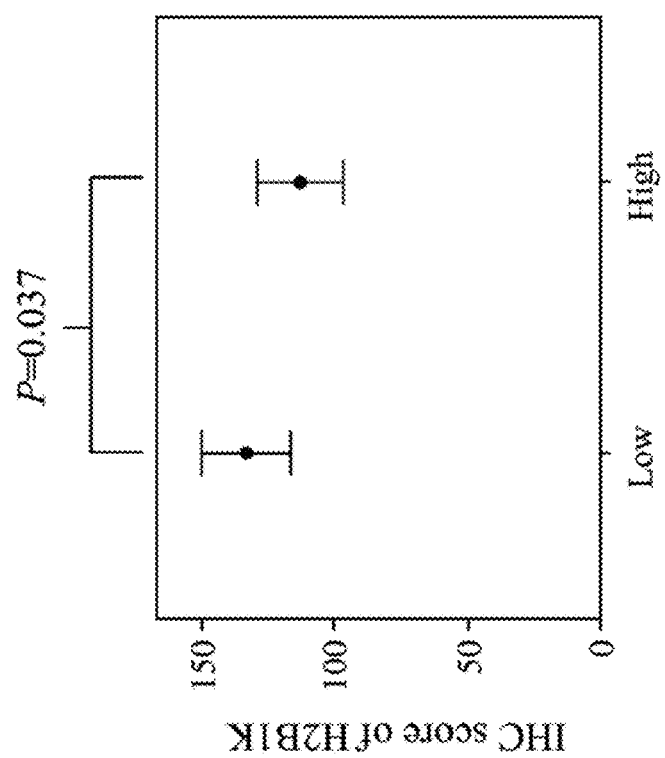
FIG. 10B is the quantification of the IHC score of the H2B1K antitrypsin expressions in high-grade UC tissue specimens and low-grade UC tissue specimens detected by the immunohistochemical staining.
Figure 10A:
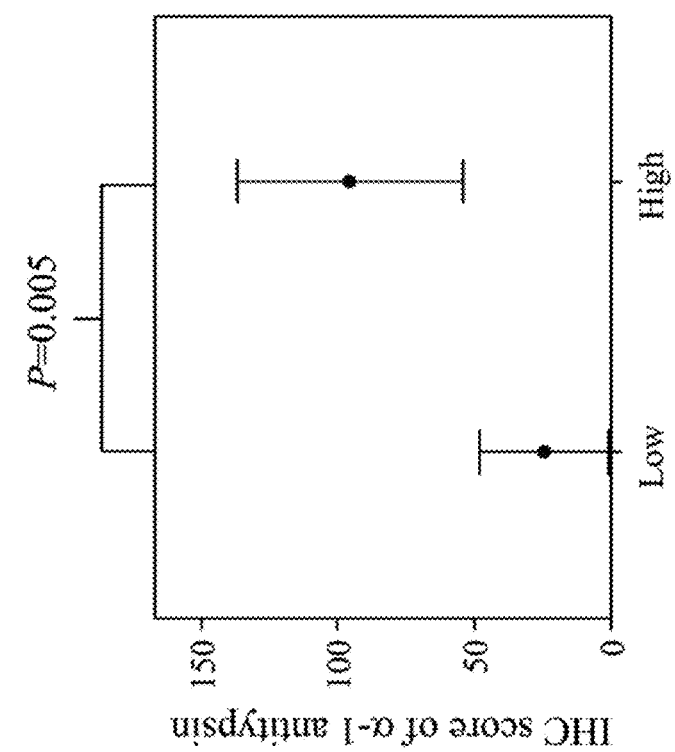
FIG. 10A is the quantification of the IHC score of the α-1 antitrypsin expressions in high-grade UC tissue specimens and low-grade UC tissue specimens detected by the immunohistochemical staining.

FIG. 9A is the quantification of the IHC score of the α-1 antitrypsin expressions in the non-UC tissue specimens and the UC tissues specimens detected by the immunohistochemical staining. FIG. 9B is the quantification of IHC score of H2B1K expressions in the non-UC tissue specimens and the UC tissues specimens detected by the immunohistochemical staining. FIG. 10A is the quantification of IHC score of the α-1 antitrypsin expressions in high-grade UC tissue specimens and low-grade UC tissue specimens detected by the immunohistochemical staining. FIG. 10B is the quantification of IHC score of the H2B1K antitrypsin expressions in high-grade UC tissue specimens and low-grade UC tissue specimens detected by the immunohistochemical staining.

In FIGS. 9A and 9B, the IHC scores for the α-1 antitrypsin are 4.40-fold higher significantly in the UC tissue specimens than in the non-UC tissue specimens (p value is 0.038). For the H2B1K expressions, the IHC score of the UC tissue specimens is up to 8.20-fold higher compared with the non-UC tissue specimens (p value is 0.005). In FIGS. 10A and 10B, the α-1 antitrypsin is highly expressed with 6.32-fold change in high grade UC tissue specimens than low grade UC tissue specimens (p value is 0.005); the expression of the H2B1K is 2.75-fold stronger in low grade UC tissue specimens compared with high grade (p value is 0.037).

Table 2 is correlations of the IHC score of the α-1 antitrypsin and the H2B1K with clinical parameters of the subjects.

TABLE 2

The correlations of the IHC socre of the α-1 antitrypsin and the H2B1K with clinical parameters of the subjects

| Normal versus UC | | | |
|---|---|---|---|
| | Normal (26) | UC (122) | P value |
| α-1 antitrypsin | 55.48 | 78.55 | 0.002* |
| H2B1K | 54.13 | 78.84 | 0.007* |

TABLE 2-continued

The correlations of the IHC socre of the α-1 antitrypsin and the H2B1K with clinical parameters of the subjects

| Gender | | | |
|---|---|---|---|
| | Female (43) | Male (79) | P value |
| α-1 antitrypsin | 53.93 | 65.62 | 0.269 |
| H2B1K | 65.59 | 59.27 | 0.079 |

| Age | | | |
|---|---|---|---|
| | <65 (19) | ≥65 (103) | P value |
| α-1 antitrypsin | 54.89 | 62.72 | 0.299 |
| H2B1K | 57.47 | 62.24 | 0.587 |

| Pathological grade of the urothelial cancer | | | |
|---|---|---|---|
| | Low (46) | High (76) | P value |
| α-1 antitrypsin | 51.73 | 67.41 | 0.005* |
| H2B1K | 70.01 | 56.35 | 0.037* |

| Tumor size | | | | |
|---|---|---|---|---|
| | <1 cm (61) | 1-3 cm (43) | ≥3 cm (18) | P value |
| α-1 antitrypsin | 53.01 | 60.78 | 92 | <0.001* |
| H2B1K | 62.28 | 62.29 | 56.03 | 0.773 |

| Number of tumors | | | |
|---|---|---|---|
| | Single (72) | Multiple (49) | P value |
| α-1 antitrypsin | 64.41 | 55.99 | 0.129 |
| H2B1K | 61.17 | 60.74 | 0.947 |

| Tumor invasion degree (T) | | | | |
|---|---|---|---|---|
| | Ta + Tis | T1 + T2 | T3 + T4 | P value |
| α-1 antitrypsin | 49.88 | 62.94 | 61.48 | 0.512 |
| H2B1K | 94.25 | 56.13 | 63.43 | 0.013* |

| Lymph node metastasis degree (N) | | | | |
|---|---|---|---|---|
| | N0 (117) | N1 (2) | N2 (2) | P value |
| α-1 antitrypsin | 59.97 | 70.25 | 111.75 | 0.046 |
| H2B1K | 60.75 | 70.5 | 66.0 | 0.907 |

| Distant metastasis degree (M) | | | |
|---|---|---|---|
| | M0 (117) | M1 (5) | P value |
| α-1 antitrypsin | 60.43 | 86.6 | 0.057 |
| H2B1K | 62.9 | 28.7 | 0.033* |

| Pathologic stage | | | | | |
|---|---|---|---|---|---|
| | 0 (7) | I + II (64) | III (38) | IV (13) | P value |
| α-1 antitrypsin | 51.29 | 61.13 | 56.07 | 84.69 | 0.021* |
| H2B1K | 95.64 | 58.06 | 62.01 | 58.54 | 0.062 |

In Table 2, the α-1 antitrypsin is significantly positively correlated with the pathological grade of the UC (p value is 0.005), the tumor size (p value is less than 0.001), and the pathologic stage (p value is 0.021). In term of the tumor size, the tissue specimens from tumor size >3 cm have the highest IHC scores of the α-1 antitrypsin, then tumor size 1-3 cm, and then tumor size <1 cm (p value is less than 0.001). The IHC scores of the α-1 antitrypsin are associated with pathologic stage of the UC. Stage 4 UC have the highest IHC expression scores of the α-1 antitrypsin then other IHC scores of other stages.

The results of the immunohistochemical staining further validate that the 5593 m/z polypeptide 250 and the 5947 m/z polypeptide 260 can be used as the biomarkers for detecting the urothelial cancer.

Figure 11:
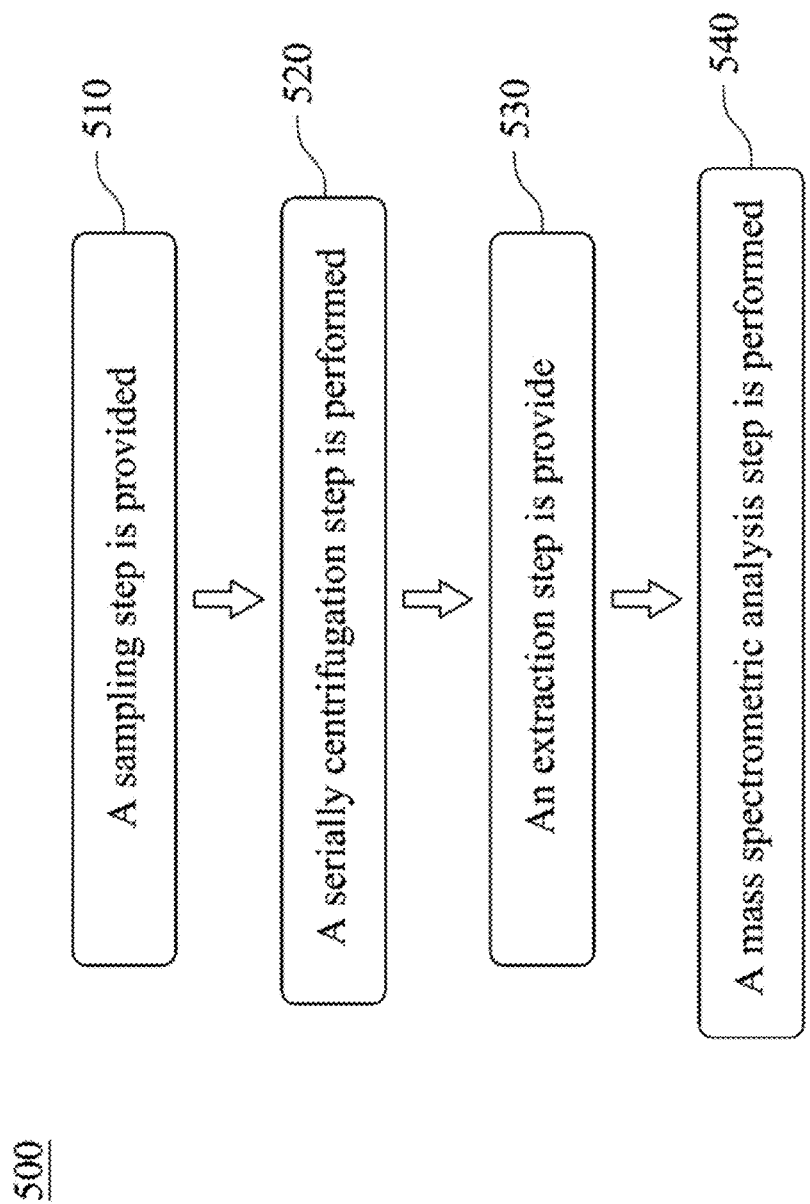
FIG. 11 is a flow diagram showing a method for predicting a recurrence and a progression of an urothelial cancer patient after a treatment according to yet another embodiment of the present disclosure.

IV. A Method for Predicting a Recurrence and a Progression of an Urothelial Cancer Patient after a Treatment of the Present Disclosure FIG. 11 is a flow diagram showing a method 500 for predicting the recurrence and the progression of the urothelial cancer patient after the treatment according to yet another embodiment of the present disclosure. The method 500 for predicting the recurrence and the progression of the urothelial cancer patient after the treatment includes a step 510, a step 520, a step 530 and a step 540.

In the step 510, a sampling step is provided. First morning urine samples are obtained from the subjects. For each urine sample (~50 ml), one protease inhibitor cocktail tablet (Roche, Mannheim, Germany) is added. The urine sample is centrifuged at 1,000×g for 10 minutes to remove debris. Then the urine sample is stored at −80° C. until subsequent serially centrifugation step or directly performed the serially centrifugation step.

In the step 520, the serially centrifugation step is performed on the urine sample, wherein the serially centrifugation step further includes steps as follows. The urine sample is centrifuged at 17,000×g for 10 minutes at 4° C. to obtain the first supernatant and the first precipitate. The first supernatant is collected in new tube, and the first precipitate is resuspended with the isolation solution (10 mm triethanolamine/250 mm sucrose, pH 7.6, 0.5 mm PMSF) before adding 200 mg/ml dithiotheritol to obtain the first mixture. The first mixture is incubated at 95° C. for 2 minutes, and then centrifuged at 17,000×g for 30 minutes at 4° C. to obtain the second supernatant and the second precipitate. The first supernatant and the second supernatant are mixed to obtain the second mixture, and the second mixture is centrifuged at 200,000×g for 1 hour at 4° C. to obtain the third precipitate.

In the step 530, the extraction step is provided. The third precipitate is resuspended with the extraction solvent to obtain the third mixture, wherein the extraction solvent is formic acid and/or acetonitrile. Further, the extraction solvent is the formic acid at the weight percentage in the range from 50% to 98% or the mixture of the formic acid at the weight percentage in the range from 25% to 50% with 50 weight percentage of the acetonitrile. Then the third mixture is centrifuged at 10,000×g for 15 minutes at 4° C. to remove the insoluble sediment and obtain the fourth supernatant.

In the step 540, the mass spectrometric analysis step is performed on the fourth supernatant by using the MALDI-TOF MS, wherein the urothelial cancer patient is determined to have a high recurrence and a high progression after the treatment when the 5947 m/z polypeptide 260 is detected in the fourth supernatant. The 5947 m/z polypeptide 260 has amino acid sequence of SEQ ID NO:6.

4.1 Probability Analysis of Overall Recurrence-Free and Overall Progression-Free In this example, 129 US patients receiving the TURBT, a cystectomy, or a nephroureterectomy are classified into the UC patient with positive 5947 m/z polypeptide expression (m/z 5947 (+)) and negative 5947 m/z polypeptide expression (m/z 5947 (−)) according to the expression level of the biomarker. Statistical analysis is further performed by using SPSS 20.0 (SPSS Inc.). A survival time is analyzed by Kaplan-Meier estimate, and a statistical significant of the survival time is further analyzed by a log rank test. A p value of <0.05 is considered statistically significant in all statistical analysis of this example.

A survival analysis is a common statistical analysis of clinical trials in various cancers, and is a statistic that deals with time variable. In more details, the survival analysis deals with analysis of time duration until one or more events happen. Two evaluation indexes of the time variable, an overall recurrence-free and an overall progression-free, are used in this example. The event is "the recurrence or a death" in the evaluation index of the overall recurrence-free, and a length of time from a subject participating in the clinical trial until the recurrence is then observed. The event is "the progression or the death" in the evaluation index of the overall progression-free, and the length of time from the subject participating in the clinical trial until the progression is then observed. A median follow-up time is 13.3 months (range, 2-32 months). At the time of analysis, the UC recurred in 80 patients (62.0%), and four patients died (3.1%). Among the deceased patients, three died of metastatic UC.

Figure 12B:
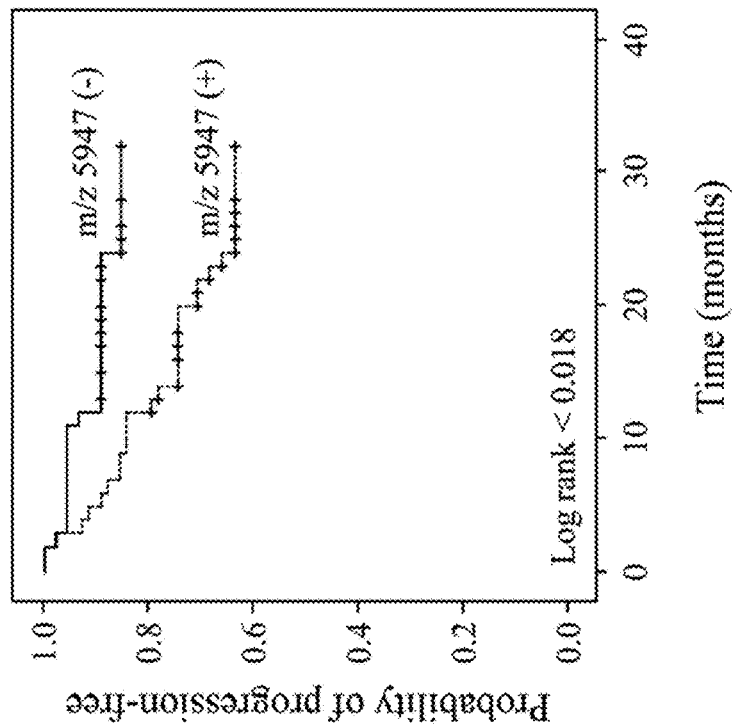
FIG. 12B is the survival curve showing overall progression-free according to yet another embodiment of the present disclosure.
Figure 12A:
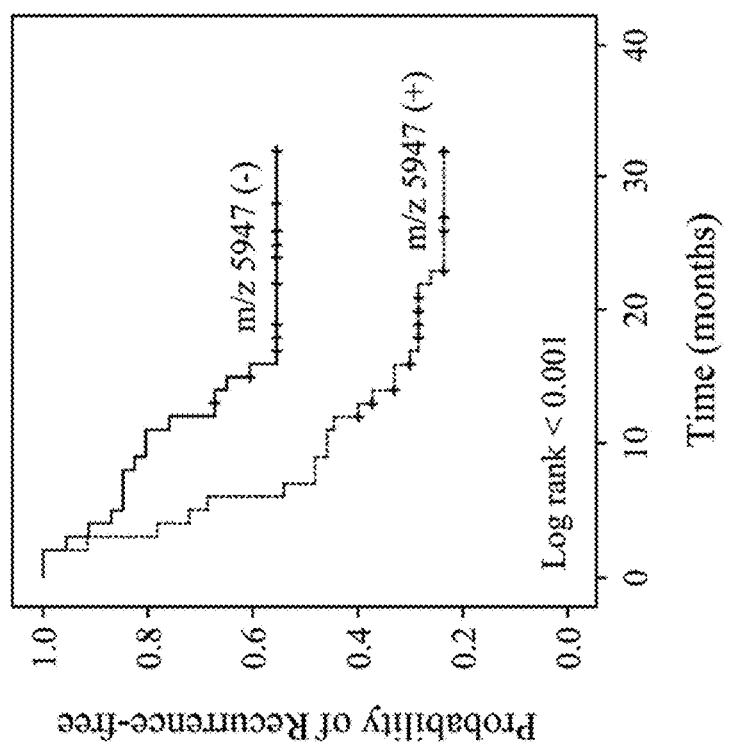
FIG. 12A is a survival curve showing overall recurrence-free according to yet another embodiment of the present disclosure.

FIG. 12A is a survival curve showing overall recurrence-free according to yet another embodiment of the present disclosure. FIG. 12B is the survival curve showing overall progression-free according to yet another embodiment of the present disclosure. A ladder in the figure represents a time point in an occurrence of the event, and a cross-mark in the figure represents the time point in the occurrence of censored data. In FIG. 12A, an overall recurrence-free time in the UC patient with negative 5947 m/z polypeptide expression is longer than that in the UC patient with positive 5947 m/z polypeptide expression. The p value analyzed by the log rank test is less than 0.001 between the UC patient with positive 5947 m/z polypeptide expression and the UC patient with negative 5947 m/z polypeptide expression. In FIG. 12B, an overall progression-free time in the UC patient with negative 5947 m/z polypeptide expression is longer than that in the UC patient with positive 5947 m/z polypeptide expression. The p value analyzed by the log rank test is 0.018 between the UC patient with positive 5947 m/z polypeptide expression and the UC patient with negative 5947 m/z polypeptide expression. These results indicate that the 5947 m/z polypeptide 260 has an important effect on predictions of the recurrence and the progression of the UC patient after the treatment.

4.2 Treatment Effect Assessment Analysis

The log rank test is only used to determine whether the differences are significant between different groups, but it can not estimate a treatment effect. Therefore, a Cox proportional hazard model is used for estimating the treatment effect according dependent variables in this example. There are two assays, an univariate regression assay and an multivariate regression assay, are performed, wherein the univariate regression assay includes one independent variable, and the multivariate regression assay includes at least two independent variables.

Table 3 is the treatment effect assessment analysis of the recurrence. When the hazard ratio is greater than 1, it indicates that the percentage of a death occurrence in the patient having the independent variable is greater than that in the patient who does not have the independent variable. Furthermore, when the HR is greater than 1 and the p value is less than 0.05, it indicates that the independent variable has a statistically significant difference. The univariate regression assay indicates that the 5947 m/z polypeptide 260 is associated with a higher risk of the recurrence of the UC (HR, 2.36; p value is 0.001). The multivariate regression assay shows that the 5947 m/z polypeptide 260 is an independent predictor of the UC recurrence (HR, 2.29; p value is 0.001). It indicates that the occurrence of the recurrence in the patient with positive 5947 m/z polypeptide expression is 2.29 times higher than that in the patient with negative 5947 m/z polypeptide expression. The results in Table 3 show that the 5947 m/z polypeptide 260 has the important effect on the prediction of the recurrence of the UC patient after the treatment.

TABLE 3

The treatment effect assessment analysis of the recurrence

| Predictors | Univariate analysis | | Multivariate analysis | |
|---|---|---|---|---|
| | HR | P value | HP | P value |
| Age (≥65 yrs vs ≤65 yrs) | 1.79 | 0.021 | 1.71 | 0.034** |
| Gender: males vs female | 1.003 | 0.99 | 1.089 | 0.722 |
| Tumor size | | | | |
| 1-3 cm vs <1 cm | 1.194 | 0.535 | 1 | 0.371 |
| ≥3 cm vs <1 cm | 1.022 | 0.933 | 1.11 | 0.794 |
| Grade: High vs Low | 1.08 | 0.754 | 1.03 | 0.909 |
| Stage | | | | |
| T2 vs Tis/Ta/T1 | 1.52 | 0.157 | 1.346 | 0.3 |
| T3/T4 vs T2 | 1.72 | 0.75 | 1.249 | 0.41 |
| Numbers of tumors: multiple vs single | 1.10 | 0.678 | 1.10 | 0.644 |
| Lymph node status: metastatsis | 2.058 | 0.16 | 1.923 | 0.206 |
| Lymphovascular invasion: positive | 1.196 | 0.609 | 1.017 | 0.963 |
| Chemotherapy*: Yes, no | 1.16 | 0.501 | 1.01 | 0.965 |
| Surgical margin: positive vs negative | 1.37 | 0.493 | 1.14 | 0.774 |
| 5947 m/z polypeptide: positive | 2.36 | 0.001 | 2.29 | 0.001** |
| 5593 m/z polypeptide: positive | 1.54 | 0.647 | 1.27 | 0.289 |

Table 4 is the treatment effect assessment analysis of the progression. The univariate regression assay indicates that the 5947 m/z polypeptide 260 is associated with the higher risk of the progression of the UC (HR, 2.77; p value is 0.025). The multivariate regression assay shows that the 5947 m/z polypeptide 260 is the independent predictor of the progression of the UC (HR, 3.11; p value is 0.039). It indicates that the occurrence of the progression in the patient with positive 5947 m/z polypeptide expression is 3.11 times higher than that in the patient with negative 5947 m/z polypeptide expression. The results in Table 4 show that the 5947 m/z polypeptide 260 has the important effect on the prediction of the progression of the UC patient after the treatment.

TABLE 4

The treatment effect assessment analysis of the progression

| Predictors | Univariate analysis | | Multivariate analysis | |
|---|---|---|---|---|
| | HR | P value | HP | P value |
| Age (≥65 yrs vs ≤65 yrs) | 2.35 | 0.046 | 2.35 | 0.096 |
| Gender: males vs female | 1.048 | 0.899 | 1.036 | 0.481 |

TABLE 4-continued

The treatment effect assessment analysis of the progression

| Predictors | Univariate analysis | | Multivariate analysis | |
|---|---|---|---|---|
| | HR | P value | HP | P value |
| Tumor size | | | | |
| 1-3 cm vs <1 cm | 5.59 | 0.02 | 5.15 | 0.031 |
| ≥3 cm vs <1 cm | 4.67 | 0.05 | 1.93 | 0.46 |
| Grade: High vs Low | 2.63 | 0.027 | 2.53 | 0.034 |
| Stage | | | | |
| T2 vs Tis/Ta/T1 | 1.08 | 0.867 | 1.07 | 0.893 |
| T3/T4 vs T2 | 1.18 | 0.686 | 1.17 | 0.385 |
| Numbers of tumors: multiple vs single | 5.58 | 0.02 | 1.568 | 0.367 |
| Lymph node status: metastatsis | 1.23 | 0.776 | 1.079 | 0.47 |
| Lymphovascular invasion: positive | 1.71 | 0.46 | 1.58 | 0.46 |
| Chemotherapy*: Yes, no | 1.54 | 0.227 | 1.42 | 0.338 |
| Surgical margin: positive vs negative | 7.58 | <0.001 | 4.13 | 0.031 |
| 5947 m/z polypeptide: positive | 2.77 | 0.025 | 3.11 | 0.039** |
| 5593 m/z polypeptide: positive | 1.156 | 0.683 | 1.222 | 0.649 |

To sum up, the method for validating the existence of the urinary exosome is provided in the present disclosure, which uses a novel extraction method to obtain an extract. The extract can be directly performed the mass spectrometric analysis step to detect the 3367 m/z polypeptide, the 3441 m/z polypeptide, the 3483 m/z polypeptide and the 10884 m/z polypeptide. When at least two polypeptides of the 3367 m/z polypeptide, the 3441 m/z polypeptide, the 3483 m/z polypeptide and the 10884 m/z polypeptide are detected in the extract, the urinary exosome is existed in the extract. It provides a platform for rapidly validating the existence of the urinary exosome, thus it can be a rapid diagnostic test for clinical and basic research. The non-invasive method for identifying an urothelial cancer is also provided in the present disclosure, which uses the novel extraction method to obtain the extract containing the urinary exosome. The extract can be directly performed the mass spectrometric analysis step to detect the 5593 m/z polypeptide and the 5947 m/z polypeptide. It provides a rapid and non-invasive method for quickly and objectively detecting whether the subject suffering from the urothelial cancer. The method for predicting the recurrence and the progression of the urothelial cancer patient after the treatment is further provided in the present disclosure, which uses the novel extraction method to obtain the extract containing the urinary exosome. The extract can be directly performed the mass spectrometric analysis step to detect the 5947 m/z polypeptide. It provides the non-invasive method for applying on a high-risk subjects with suspected urothelial cancer. Therefore, the physician can determine whether the UC patient need to treat with other drugs or other treatment plans to enhance the overall survival time and the disease free survival time in the clinical application.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A non-invasive method for identifying an urothelial cancer, comprising:
   providing a sampling step, wherein a urine sample is obtained from a subject;
   performing a serially centrifugation step on the urine sample, comprising:
      centrifuging the urine sample to obtain a first supernatant and a first precipitate;
      resuspending the first precipitate with an isolation solution to obtain a first mixture, and centrifuging the first mixture to obtain a second supernatant and a second precipitate; and
      mixing the first supernatant and the second supernatant to obtain a second mixture, and centrifuging the second mixture to obtain a third precipitate;
   providing an extraction step, wherein the third precipitate is resuspended with an extraction solvent to obtain a third mixture, the third mixture is centrifuged to obtain a fourth supernatant, and the extraction solvent is formic acid and/or acetonitrile; and
   performing a mass spectrometric analysis step on the fourth supernatant by using a matrix-assisted laser desorption ionization-time of flight mass spectrometry (MALDI-TOF MS) to detect whether the fourth supernatant has a 5593 m/z polypeptide and/or a 5947 m/z polypeptide.

2. The non-invasive method for identifying the urothelial cancer of claim 1, wherein the extraction solvent is the formic acid at a weight percentage in a range from 50% to 98%.

3. The non-invasive method for identifying the urothelial cancer of claim 2, wherein the extraction solvent is 75 weight percentage of the formic acid.

4. The non-invasive method for identifying the urothelial cancer of claim 1, wherein the extraction solvent is a mixture of the formic acid at the weight percentage in the range from 25% to 50% with 50 weight percentage of the acetonitrile.

5. The non-invasive method for identifying the urothelial cancer of claim 1, wherein the 5593 m/z polypeptide has amino acid sequence of SEQ ID NO:5.

6. The non-invasive method for identifying the urothelial cancer of claim 1, wherein the 5947 m/z polypeptide has amino acid sequence of SEQ ID NO:6.

* * * * *